US012582106B2

(12) United States Patent
Ju et al.

(10) Patent No.: US 12,582,106 B2
(45) Date of Patent: Mar. 24, 2026

(54) IL-15 HUMANIZED MOUSE MODEL AND USE THEREOF

(71) Applicant: GEMPHARMATECH CO., LTD., Nanjing (CN)

(72) Inventors: Cunxiang Ju, Nanjing (CN); Weiwei Yu, Nanjing (CN); Mingkun Zhang, Nanjing (CN); Hongyan Sun, Nanjing (CN); Dingyu Wang, Nanjing (CN)

(73) Assignee: GEMPHARMATECH CO., LTD., Jiangsu (CN)

( * ) Notice: Subject to any disclaimer, the term of this patent is extended or adjusted under 35 U.S.C. 154(b) by 1031 days.

(21) Appl. No.: 17/764,791

(22) PCT Filed: Dec. 24, 2020

(86) PCT No.: PCT/CN2020/139153
§ 371 (c)(1),
(2) Date: Mar. 29, 2022

(87) PCT Pub. No.: WO2021/129766
PCT Pub. Date: Jul. 1, 2021

(65) Prior Publication Data
US 2022/0354097 A1    Nov. 10, 2022

(30) Foreign Application Priority Data
Dec. 25, 2019    (CN) .......................... 201911360623.9

(51) Int. Cl.
| | |
|---|---|
| *A01K 67/0278* | (2024.01) |
| *A01K 67/027* | (2024.01) |
| *A01K 67/0275* | (2024.01) |
| *A61K 49/00* | (2006.01) |
| *A61P 35/00* | (2006.01) |
| *C07K 14/54* | (2006.01) |
| *C12N 15/113* | (2010.01) |
| *C12N 15/62* | (2006.01) |
| *C12N 15/89* | (2006.01) |
| *C12N 15/90* | (2006.01) |

(52) U.S. Cl.
CPC ........ *A01K 67/0278* (2013.01); *A01K 67/027* (2013.01); *A01K 67/0275* (2013.01); *A61K 49/00* (2013.01); *A61K 49/0008* (2013.01); *C07K 14/54* (2013.01); *C07K 14/5443* (2013.01); *C12N 15/625* (2013.01); *C12N 15/89* (2013.01); *C12N 15/907* (2013.01); *A61P 35/00* (2018.01); *C12N 15/1136* (2013.01)

(58) Field of Classification Search
CPC ........... A01K 67/027; A01K 2217/072; A01K 2217/15; A01K 2227/105; A01K 2267/02; A01K 2267/0368; A01K 67/0275; A61K 49/00; A61K 49/0008; A61P 35/00; C07K 14/54; C07K 14/5443; C12N 15/1136; C12N 2310/20

USPC ....... 435/325, 354; 536/23.4, 23.5; 530/351; 800/3, 9, 10, 18, 25
See application file for complete search history.

(56) References Cited

U.S. PATENT DOCUMENTS

2015/0106961 A1*  4/2015  Rojas ................. A01K 67/0278
800/9

FOREIGN PATENT DOCUMENTS

| CN | 105744829 A | 7/2016 |
|---|---|---|
| CN | 107896479 A | 4/2018 |
| CN | 109266656 A | 1/2019 |
| WO | 2015057758 A1 | 4/2015 |
| WO | 2016168212 A1 | 10/2016 |

OTHER PUBLICATIONS

Anderson 1995, Genomics, 25, 701-706. (Year: 1995).*
Branch 2017, Pharmas Almanac, Charles River Announces NCG Mouse Model, published Apr. 5, 2017, retrieved Mar. 11, 2025 from the Internet: <https://www.pharmasalmanac.com/articles/charles-river-announces-ncg-mouse-model>. (Year: 2017).*
Liu et al. 2017, EMBO Reports, 18(2), 187-193. (Year: 2017).*
GenBank 2010 (5UTR mRNA), published Oct. 6, 2010, retrieved on Mar. 12, 2025 from the Internet: < https://www.ncbi.nlm.nih.gov/nucleotide/AK155616.1?report=genbank&log$=nuclalign&blast_rank=1&RID=X4E7GVYM016&from=2&to=1144>. (Year: 2010).*
GenBank 1995 (signal mRNA), published Sep. 14, 1995, retrieved on Mar. 12, 2025 from the Internet: <https://www.ncbi.nlm.nih.gov/nucleotide/U14332.1?report=genbank&log$=nuclalign&blast_rank=60&RID=X45V9FPK016>. (Year: 1995).*
GenBank 2005 (5UTR genomic), published Jul. 23, 2005, retrieved on Mar. 11, 2025 from the Internet: <https://www.ncbi.nlm.nih.gov/nucleotide/AC156993.3?report=genbank&log$=nuclalign&blast_rank=4&RID=X1UK78U2016&from=90945&to=91877>. (Year: 2005).*

(Continued)

*Primary Examiner* — Anne Marie S Wehbe
*Assistant Examiner* — Katie L Pennington
(74) *Attorney, Agent, or Firm* — Sughrue Mion, PLLC

(57) ABSTRACT

Provided are a mouse and a functional activity part thereof, comprising a humanized IL-15 gene; the humanized IL-15 gene comprises a human IL-15 gene segment and a mouse IL-15 gene segment, the human IL-15 gene segment comprises at least a part of exon 4, exon 5, exon 6, exon 7 and exon 8 of the human IL-15 gene, and the mouse IL-15 gene segment comprises exon 1, exon 2 and exon 3 of the mouse IL-15 gene. Also provided are a preparation method and use of the mouse.

16 Claims, 11 Drawing Sheets
Specification includes a Sequence Listing.

(56)     References Cited

OTHER PUBLICATIONS

GenBank 2005 (signal genomic), published Jul. 23, 2005, retrieved on Mar. 12, 2025 from the Internet: <https://www.ncbi.nlm.nih.gov/nucleotide/AC156993.3?report=genbank&log$=nuclalign&blast_rank=1&RID=X455RP0B013&from=33083&to=33169>. (Year: 2005).*

Steel et al. 2012, Trends in Pharmacological Sciences, 33(1), 35-41.*

PCT/CN2020/139153 International Search Report dated Mar. 25, 2021.

* cited by examiner

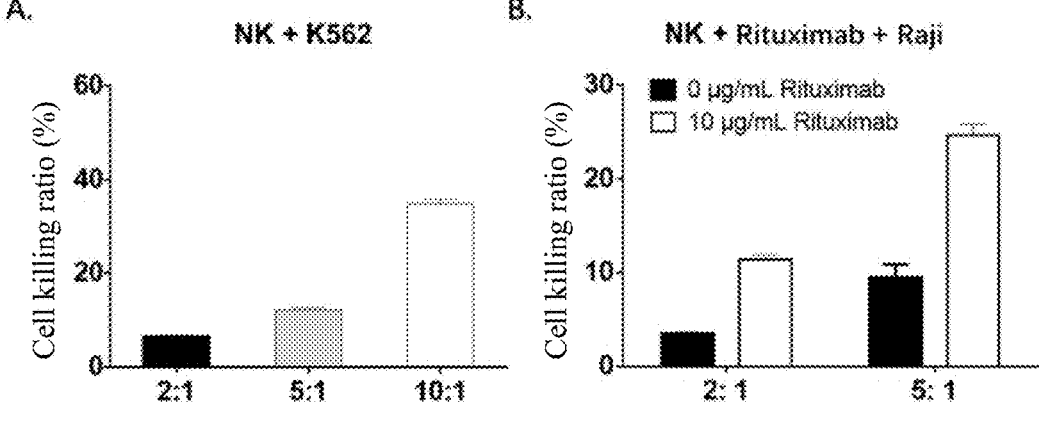
Fig. 12
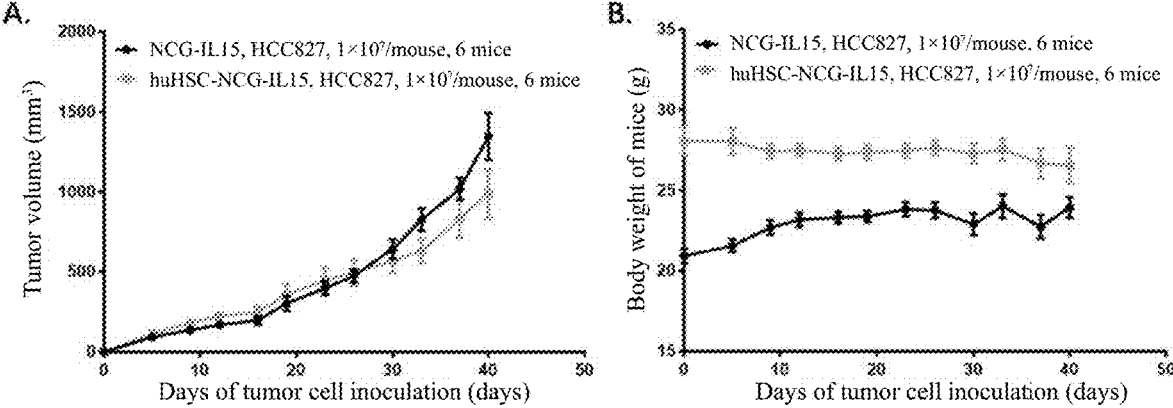
Fig. 13A-B

```
                          SEQUENCE LISTING

<160> NUMBER OF SEQ ID NOS: 32

<210> SEQ ID NO 1
<211> LENGTH: 432
<212> TYPE: DNA
<213> ORGANISM: Artificial Sequence
<220> FEATURE:
<223> OTHER INFORMATION: Human IL-15 gene segment

<400> SEQUENCE: 1
cttctaaaca gtcattttct aactgaagct ggcattcatg tcttcatttt gggctgtttc       60
agtgcagggc ttcctaaaac agaagccaac tgggtgaatg taataagtga tttgaaaaaa      120
attgaagatc ttattcaatc tatgcatatt gatgctactt tatatacgga aagtgatgtt      180
cacccaagtt gcaaagtaac agcaatgaag tgctttctct tggagttaca agttatttca      240
cttgagtccg gagatgcaag tattcatgat acagtagaaa atctgatcat cctagcaaac      300
aacagtttgt cttctaatgg gaatgtaaca gaatctggat gcaaagaatg tgaggaactg      360
gaggaaaaaa atattaaaga atttttgcag agttttgtac atattgtcca aatgttcatc      420
aacacttctt ga                                                         432

<210> SEQ ID NO 2
<211> LENGTH: 632
<212> TYPE: DNA
<213> ORGANISM: Artificial Sequence
<220> FEATURE:
<223> OTHER INFORMATION: Humanized IL-15 gene targeting fragment

<400> SEQUENCE: 2
tccatgtttt taactagaga tgttttacca ttttgtctac atttatgttt tccagaaacc       60
atatatgagg aatacatcca tctcgtgcta cttgtgtttc cttctaaaca gtcattttct      120
aactgaagct ggcattcatg tcttcatttt gggctgtttc agtgcagggc ttcctaaaac      180
agaagccaac tgggtgaatg taataagtga tttgaaaaaa attgaagatc ttattcaatc      240
tatgcatatt gatgctactt tatatacgga aagtgatgtt cacccaagtt gcaaagtaac      300
agcaatgaag tgctttctct tggagttaca agttatttca cttgagtccg gagatgcaag      360
tattcatgat acagtagaaa atctgatcat cctagcaaac aacagtttgt cttctaatgg      420
gaatgtaaca gaatctggat gcaaagaatg tgaggaactg gaggaaaaaa atattaaaga      480
atttttgcag agttttgtac atattgtcca aatgttcatc aacacttctt gactgcatgc      540
gagcctcttc cgtgtttctg ttattaaggt acctccacct gctgctcaga ggcagcacag      600
ctccatgcat ttgaaatctg ctgggcaaac ta                                   632

<210> SEQ ID NO 3
<211> LENGTH: 87
<212> TYPE: DNA
<213> ORGANISM: Artificial Sequence
<220> FEATURE:
<223> OTHER INFORMATION: Signal peptide gene of humanized IL-15 gene

<400> SEQUENCE: 3
ctagagatgt tttaccattt tgtctacatt tatgttttcc agaaaccata tatgaggaat       60
acatccatct cgtgctactt gtgtttc                                          87
```

-continued

```
<210> SEQ ID NO 4
<211> LENGTH: 1142
<212> TYPE: DNA
<213> ORGANISM: Artificial Sequence
<220> FEATURE:
<223> OTHER INFORMATION: 5 'UTR gene of humanized IL-15 gene

<400> SEQUENCE: 4
acagtctctg tccagatctc ctccgggctt ctatggggaa gccaaactgc ctccctgcaa       60
ggccagttgc tgtagatgca agcaacctgt gaactcaggc caactccttg aaacttcaca      120
gaggcaaagg cattccagga cacacagagg ctgtggccaa ctgcccaggg ggaggagact      180
gctctctgct ctcagttgcc cttcaggttc tgcgccctgg ggacctggca gtggcagaat      240
catgtgggca cctggtaagg tggccgggac catgtgttcc tcccgcaacc tccccagggt      300
gttgatctcc gcctcagctt gggctctttc tctttcactt ttctgttagc tggggttggg      360
actccccggc tggaaagcac tggggaaac cggggaaacc ccagctgatt cgctccttgt      420
gccttgattg ctcccgctgg ctgctgccct gcatcctgca cccttcaacc agaacccgat      480
ggaggtacag aatgggaggt ggtagtgctg gtggtggtgg atcaacaatg gaattttttt      540
tttttccgaa agcctacgcc ccgggcccct cccagctctg gctctgctca ggcaccctt      600 tcccctccag ctgccggcca ggccgccccg ccctctttct tgaccaagac ttcaatactc      660
agtggcactg tattcccctt ctgtccagcc actcttcccc agagttctct tcttcatcct      720 ccccccttgca gagtagggca gcttgcaggt cctcctgcaa gtctctccca attctctgcg      780
cccaaaagac ttgcagtgca tctccttacg cgctgcaggg accttgccag ggcaggactg      840
cccccgccca gttgcagagt tggacgaaga cgggatcctg ctgtgtttgg aaggctgagt      900
tccacatcta acagctcaga gaggtcagga aagaatccac cttgacacat ggccctctgg      960
ctcttcaaag cactgcctct tcatggtcct tgctggtgag gtccttaaga acacagaaac     1020
ccatgtcagc agataaccag cctacaggag gccaagaaga gttctggatg gatggcagct     1080
ggaagcccat cgccatagcc agctcatctt caacattgaa gctcttacct gggcattaag     1140
ta                                                                    1142

<210> SEQ ID NO 5
<211> LENGTH: 277
<212> TYPE: DNA
<213> ORGANISM: Artificial Sequence
<220> FEATURE:
<223> OTHER INFORMATION: 3 'UTR gene of humanized IL-15 gene

<400> SEQUENCE: 5
ctgcatgcga gcctcttccg tgtttctgtt attaaggtac ctccacctgc tgctcagagg       60
cagcacagct ccatgcattt gaaatctgct gggcaaacta agcttcctaa caaggagata      120
atgagccact tggatcacat gaaatcttgg aaatgaagag aggaaaagag ctcgtctcag      180
acttattttt gcttgcttat ttttaattta ttgcttcatt tgtacatatt tgtaatataa      240
cagaagatgt ggaataaagt tgtatggata ttttatc                               277

<210> SEQ ID NO 6
<211> LENGTH: 489
<212> TYPE: DNA
<213> ORGANISM: Artificial Sequence
<220> FEATURE:
<223> OTHER INFORMATION: IL-15 gene of wild-type mice (IL-15 is not
      humanized)
```

```
<400> SEQUENCE: 6
atgaaaattt tgaaaccata tatgaggaat acatccatct cgtgctactt gtgtttcctt      60
ctaaacagtc acttttaac tgaggctggc attcatgtct tcattttggg ctgtgtcagt       120
gtaggtctcc ctaaaacaga ggccaactgg atagatgtaa gatatgacct ggagaaaatt      180
gaaagcctta ttcaatctat tcatattgac accactttat acactgacag tgactttcat      240
cccagttgca aagttactgc aatgaactgc tttctcctgg aattgcaggt tattttacat      300
gagtacagta acatgactct taatgaaaca gtaagaaacg tgctctacct tgcaaacagc      360
actctgtctt ctaacaagaa tgtagcagaa tctggctgca aggaatgtga ggagctggag      420
gagaaaacct tcacagagtt tttgcaaagc tttatacgca ttgtccaaat gttcatcaac      480
acgtcctga                                                             489
```

```
<210> SEQ ID NO 7
<211> LENGTH: 143
<212> TYPE: PRT
<213> ORGANISM: Artificial Sequence
<220> FEATURE:
<223> OTHER INFORMATION: Protein encoded by human IL-15 gene segment

<400> SEQUENCE: 7

Leu Leu Asn Ser His Phe Leu Thr Glu Ala Gly Ile His Val Phe Ile
1               5                   10                  15

Leu Gly Cys Phe Ser Ala Gly Leu Pro Lys Thr Glu Ala Asn Trp Val
            20                  25                  30

Asn Val Ile Ser Asp Leu Lys Lys Ile Glu Asp Leu Ile Gln Ser Met
        35                  40                  45

His Ile Asp Ala Thr Leu Tyr Thr Glu Ser Asp Val His Pro Ser Cys
    50                  55                  60

Lys Val Thr Ala Met Lys Cys Phe Leu Leu Glu Leu Gln Val Ile Ser
65                  70                  75                  80

Leu Glu Ser Gly Asp Ala Ser Ile His Asp Thr Val Glu Asn Leu Ile
                85                  90                  95

Ile Leu Ala Asn Asn Ser Leu Ser Ser Asn Gly Asn Val Thr Glu Ser
                100                 105                 110

Gly Cys Lys Glu Cys Glu Glu Leu Glu Glu Lys Asn Ile Lys Glu Phe
            115                 120                 125

Leu Gln Ser Phe Val His Ile Val Gln Met Phe Ile Asn Thr Ser
        130                 135                 140
```

```
<210> SEQ ID NO 8
<211> LENGTH: 162
<212> TYPE: PRT
<213> ORGANISM: Artificial Sequence
<220> FEATURE:
<223> OTHER INFORMATION: IL-15 protein in humanized mice

<400> SEQUENCE: 8

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60
```

```
Gln Ser Met His Ile Asp Ala Thr Leu Tyr Thr Glu Ser Asp Val His
65              70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
                100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
        130                 135                 140

Lys Glu Phe Leu Gln Ser Phe Val His Ile Val Gln Met Phe Ile Asn
145                 150                 155                 160

Thr Ser

<210> SEQ ID NO 9
<211> LENGTH: 162
<212> TYPE: PRT
<213> ORGANISM: Artificial Sequence
<220> FEATURE:
<223> OTHER INFORMATION: IL-15 protein in wild-type mice (IL-15 is not
      humanized)

<400> SEQUENCE: 9

Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
                20                  25                  30

Val Phe Ile Leu Gly Cys Val Ser Val Gly Leu Pro Lys Thr Glu Ala
            35                  40                  45

Asn Trp Ile Asp Val Arg Tyr Asp Leu Glu Lys Ile Glu Ser Leu Ile
        50                  55                  60

Gln Ser Ile His Ile Asp Thr Thr Leu Tyr Thr Asp Ser Asp Phe His
65              70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
                100                 105                 110

Asn Val Leu Tyr Leu Ala Asn Ser Thr Leu Ser Ser Asn Lys Asn Val
            115                 120                 125

Ala Glu Ser Gly Cys Lys Glu Cys Glu Glu Leu Glu Glu Lys Thr Phe
        130                 135                 140

Thr Glu Phe Leu Gln Ser Phe Ile Arg Ile Val Gln Met Phe Ile Asn
145                 150                 155                 160

Thr Ser

<210> SEQ ID NO 10
<211> LENGTH: 20
<212> TYPE: DNA
<213> ORGANISM: Artificial Sequence
<220> FEATURE:
<223> OTHER INFORMATION: IL15-5S1

<400> SEQUENCE: 10
gcattcatgt cttcattttg                                           20

<210> SEQ ID NO 11
<211> LENGTH: 20
<212> TYPE: DNA
```

-continued

```
<213> ORGANISM: Artificial Sequence
<220> FEATURE:
<223> OTHER INFORMATION: IL15-5S2

<400> SEQUENCE: 11
tggcattcat gtcttcattt                                              20

<210> SEQ ID NO 12
<211> LENGTH: 20
<212> TYPE: DNA
<213> ORGANISM: Artificial Sequence
<220> FEATURE:
<223> OTHER INFORMATION: IL15-3S1

<400> SEQUENCE: 12
aggacgtgtt gatgaacatt                                              20

<210> SEQ ID NO 13
<211> LENGTH: 20
<212> TYPE: DNA
<213> ORGANISM: Artificial Sequence
<220> FEATURE:
<223> OTHER INFORMATION: IL15-3S2

<400> SEQUENCE: 13
gctttgcaaa aactctgtga                                              20

<210> SEQ ID NO 14
<211> LENGTH: 23
<212> TYPE: DNA
<213> ORGANISM: Artificial Sequence
<220> FEATURE:
<223> OTHER INFORMATION: 710022-IL15-5S1F

<400> SEQUENCE: 14
atagcattca tgtcttcatt ttg                                          23

<210> SEQ ID NO 15
<211> LENGTH: 23
<212> TYPE: DNA
<213> ORGANISM: Artificial Sequence
<220> FEATURE:
<223> OTHER INFORMATION: 710022-IL15-5S1R

<400> SEQUENCE: 15
aaaccaaaat gaagacatga atg                                          23

<210> SEQ ID NO 16
<211> LENGTH: 22
<212> TYPE: DNA
<213> ORGANISM: Artificial Sequence
<220> FEATURE:
<223> OTHER INFORMATION: 710022-IL15-5S2F

<400> SEQUENCE: 16
ataggcattc atgtcttcat tt                                           22

<210> SEQ ID NO 17
<211> LENGTH: 22
<212> TYPE: DNA
<213> ORGANISM: Artificial Sequence
<220> FEATURE:
<223> OTHER INFORMATION: 710022-IL15-5S2R

<400> SEQUENCE: 17
aaacaaatga agacatgaat gc                                           22
```

-continued

```
<210> SEQ ID NO 18
<211> LENGTH: 22
<212> TYPE: DNA
<213> ORGANISM: Artificial Sequence
<220> FEATURE:
<223> OTHER INFORMATION: 710022-IL15-3S1F

<400> SEQUENCE: 18
ataggacgtg ttgatgaaca tt                                              22

<210> SEQ ID NO 19
<211> LENGTH: 22
<212> TYPE: DNA
<213> ORGANISM: Artificial Sequence
<220> FEATURE:
<223> OTHER INFORMATION: 710022-IL15-3S1R

<400> SEQUENCE: 19
aaacaatgtt catcaacacg tc                                              22

<210> SEQ ID NO 20
<211> LENGTH: 23
<212> TYPE: DNA
<213> ORGANISM: Artificial Sequence
<220> FEATURE:
<223> OTHER INFORMATION: 710022-IL15-3S2F

<400> SEQUENCE: 20
atagctttgc aaaaactctg tga                                             23

<210> SEQ ID NO 21
<211> LENGTH: 23
<212> TYPE: DNA
<213> ORGANISM: Artificial Sequence
<220> FEATURE:
<223> OTHER INFORMATION: 710022-IL15-3S2R

<400> SEQUENCE: 21
aaactcacag agtttttgca aag                                             23

<210> SEQ ID NO 22
<211> LENGTH: 24
<212> TYPE: DNA
<213> ORGANISM: Artificial Sequence
<220> FEATURE:
<223> OTHER INFORMATION: 710022-IL15-5tF1

<400> SEQUENCE: 22
cagtatgcct gtattctttg tgcc                                            24

<210> SEQ ID NO 23
<211> LENGTH: 24
<212> TYPE: DNA
<213> ORGANISM: Artificial Sequence
<220> FEATURE:
<223> OTHER INFORMATION: 710022-IL15-5tR1

<400> SEQUENCE: 23
ctccaagaga aagcacttca ttgc                                            24

<210> SEQ ID NO 24
<211> LENGTH: 20
<212> TYPE: DNA
<213> ORGANISM: Artificial Sequence
<220> FEATURE:
```

<223> OTHER INFORMATION: 710022-IL15-3tF1

<400> SEQUENCE: 24
tgtttcagtg cagggcttcc                                                          20

<210> SEQ ID NO 25
<211> LENGTH: 21
<212> TYPE: DNA
<213> ORGANISM: Artificial Sequence
<220> FEATURE:
<223> OTHER INFORMATION: 710022-IL15-3tR1

<400> SEQUENCE: 25
cagctttcca aagatgctgg g                                                        21

<210> SEQ ID NO 26
<211> LENGTH: 20
<212> TYPE: DNA
<213> ORGANISM: Artificial Sequence
<220> FEATURE:
<223> OTHER INFORMATION: 710022-IL15-3seqR1

<400> SEQUENCE: 26
cgtgaaagac taatgtaaac                                                          20

<210> SEQ ID NO 27
<211> LENGTH: 20
<212> TYPE: DNA
<213> ORGANISM: Artificial Sequence
<220> FEATURE:
<223> OTHER INFORMATION: 710022-IL15-WT-TF1

<400> SEQUENCE: 27
catgtcagtg gcgatgaacc                                                          20

<210> SEQ ID NO 28
<211> LENGTH: 22
<212> TYPE: DNA
<213> ORGANISM: Artificial Sequence
<220> FEATURE:
<223> OTHER INFORMATION: 710022-IL15-WT-TR1

<400> SEQUENCE: 28
acaaggcttg gcacagagta gc                                                       22

<210> SEQ ID NO 29
<211> LENGTH: 25
<212> TYPE: DNA
<213> ORGANISM: Artificial Sequence
<220> FEATURE:
<223> OTHER INFORMATION: mIL15-RT-qTF1

<400> SEQUENCE: 29
tgcaaacagc actctgtctt ctaac                                                    25

<210> SEQ ID NO 30
<211> LENGTH: 25
<212> TYPE: DNA
<213> ORGANISM: Artificial Sequence
<220> FEATURE:
<223> OTHER INFORMATION: mIL15-RT-qTR1

<400> SEQUENCE: 30
gtgttgatga acatttggac aatgc                                                    25

-continued

```
<210> SEQ ID NO 31
<211> LENGTH: 22
<212> TYPE: DNA
<213> ORGANISM: Artificial Sequence
<220> FEATURE:
<223> OTHER INFORMATION: hIL15-RT-qTF1

<400> SEQUENCE: 31
acagaagcca actgggtgaa tg                                             22

<210> SEQ ID NO 32
<211> LENGTH: 25
<212> TYPE: DNA
<213> ORGANISM: Artificial Sequence
<220> FEATURE:
<223> OTHER INFORMATION: hIL15-RT-qTR1

<400> SEQUENCE: 32
aagcacttca ttgctgttac tttgc                                         25
```

IL-15 HUMANIZED MOUSE MODEL AND USE THEREOF

CROSS-REFERENCE TO RELATED APPLICATIONS

This application is a National Stage Application and claims priority under 35 U.S.C. § 371 to Patent Cooperation Treaty application PCT/CN2020/139153, filed Dec. 24, 2020, which claims the benefit of Chinese application 201911360623.9, filed Dec. 25, 2019. Priority is claimed to these applications and the disclosure of these prior applications is considered part of the disclosure of this application and to the extent allowed the entire contents of the aforementioned applications are incorporated herein.

SEQUENCE LISTING

This application incorporates by reference in its entirety the Sequence Listing entitled "2022-03-16 262790-507372 ST25.txt", is 14.088 bytes in size and was created on Mar. 16, 2022, and filed electronically herewith.

FIELD OF THE INVENTION

The present application relates to the field of biomedicine, and specifically to an IL-15 humanized mouse model and a use thereof.

BACKGROUND OF THE INVENTION

Under normal circumstances, the immune system, as an important defense weapon of the body, can maintain the body's homeostasis by recognizing and eliminating antigenic foreign substances and coordinating with other systems. Once the immune system is out of control, diseases including autoimmune diseases, tumors, infections, and metabolic diseases will sweep through the human body, which will be fatal to human health.

Research on the immune system involves a wide range of aspects, and due to ethical constraints, scientific research usually focuses on large mammals and small rodents. Rodents, as the most widely used experimental small animal models, have become indispensable alternative models in human immunity research. However, due to species specificity, conclusions obtained from rodent models cannot be directly extrapolated to the human immune system.

In view of this, it is desirable to obtain an animal model for reconstitution of a humanized immune system, to better study humanized immune cell development and related drug screening.

SUMMARY OF THE INVENTION

In one aspect, the present application provides a mouse or a functionally active part thereof, comprising a humanized IL-15 gene, wherein the humanized IL-15 gene comprises a human IL-15 gene segment and a mouse IL-15 gene segment, wherein the human IL-15 gene segment comprises at least a part of exon 4, exon 5, exon 6, exon 7, and exon 8 of the human IL-15 gene, wherein the mouse IL-15 gene segment comprises exon 1, exon 2 and exon 3 of the mouse IL-15 gene.

In some embodiments, the mouse IL-15 gene segment further comprises a regulatory sequence of the mouse IL-15 gene.

In some embodiments, the exons in the human IL-15 gene segment are composed of at least a part of exon 4, exon 5, exon 6, exon 7 and exon 8 of the human IL-15 gene.

In some embodiments, the human IL-15 gene segment comprises a nucleic acid sequence as shown in SEQ ID NO: 1.

In some embodiments, the mouse is an NCG mouse.

In some embodiments, the mouse IL-15 gene segment comprises a nucleotide sequence encoding a signal peptide of the mouse IL-15.

In some embodiments, the nucleotide sequence encoding the signal peptide of the mouse IL-15 comprises a nucleotide sequence as shown in SEQ ID NO: 3.

In some embodiments, the mouse IL-15 gene segment comprises a nucleotide sequence encoding 5'UTR.

In some embodiments, the nucleotide sequence encoding 5'UTR comprises a nucleotide sequence as shown in SEQ ID NO: 4.

In some embodiments, the mouse IL-15 gene segment comprises a nucleotide sequence encoding 3'UTR.

In some embodiments, the nucleotide sequence encoding 3'UTR comprises a nucleotide sequence as shown in SEQ ID NO: 5.

In another aspect, the present application provides an offspring of the mouse or a functionally active part thereof, wherein the offspring or the functionally active part thereof comprises a humanized IL-15 gene, the humanized IL-15 gene comprises a human IL-15 gene segment and a mouse IL-15 gene segment, the human IL-15 gene segment comprises at least a part of exon 4, exon 5, exon 6, exon 7, and exon 8 of the human IL-15 gene, the mouse IL-15 gene segment comprises exon 1, exon 2 and exon 3 of the mouse IL-15 gene.

In another aspect, the present application provides a cell line or a primary cell culture, which is derived from the mouse or the functionally active part thereof; or derived from the offspring of the mouse.

In another aspect, the present application provides a tissue, which is derived from the mouse or the functionally active part thereof; or derived from the offspring of the mouse.

In some embodiments, the tissue comprises body fluid of the mouse or the offspring of the mouse.

In some embodiments, the body fluid is selected from a group consisting of: blood, plasma, serum, urine, sweat, tear, saliva, semen, and cerebrospinal fluid.

In some embodiments, the tissue is selected from a group consisting of: epithelial tissue, connective tissue, nerve tissue and muscle tissue.

In another aspect, the present application provides a cell, which is derived from the mouse or the functionally active part thereof; or derived from the offspring of the mouse.

In some embodiments, the cell is selected from a group consisting of: epithelial cells, nerve cells, erythrocytes, leukocytes, platelets, phagocytes, B lymphocytes, effector B cells, memory B cells, T lymphocytes, memory T cells, effector T cells, NK cells, dendritic cells, granulocytes, hemocytes, myocardial cells, smooth muscle cells, skeletal muscle cells, myocardial cells, osteoblasts, neurogliocytes, liver cells, renal cells, gland cells and endocrine cells.

In some embodiments, the cell cannot develop into an intact mouse.

In another aspect, the present application provides a preparation method of a genetically modified mouse, the method comprises:

replacing a mouse IL-15 gene segment encoding a mature mouse IL-15 polypeptide on an endogenous mouse IL-15 locus with a human IL-15 gene segment encoding a mature human IL-15 polypeptide to form a humanized IL-15 gene, wherein the human IL-15 gene segment comprises at least a part of exon 4, exon 5, exon 6, exon 7, and exon 8 of the human IL-15 gene.

In some embodiments, the mouse IL-15 gene segment comprises exon 1, exon 2 and exon 3 of the mouse IL-15 gene.

In some embodiments, the mouse IL-15 gene segment further comprises a regulatory sequence of the mouse IL-15 gene.

In some embodiments, the exons in the human IL-15 gene segment are composed of at least a part of exon 4, exon 5, exon 6, exon 7 and exon 8 of the human IL-15 gene.

In some embodiments, the human IL-15 gene segment comprises a nucleic acid sequence as shown in SEQ ID NO: 1.

In some embodiments, the mouse is an NCG mouse.

In some embodiments, the mouse IL-15 gene segment comprises a nucleotide sequence encoding a signal peptide of the mouse IL-15.

In some embodiments, the nucleotide sequence encoding a signal peptide of the mouse IL-15 comprises a nucleotide sequence as shown in SEQ ID NO: 3.

In some embodiments, the mouse IL-15 gene segment comprises a nucleotide sequence encoding 5'UTR.

In some embodiments, the nucleotide sequence encoding 5'UTR comprises a nucleotide sequence as shown in SEQ ID NO: 4.

In some embodiments, the mouse IL-15 gene segment comprises a nucleotide sequence encoding 3'UTR.

In some embodiments, the nucleotide sequence encoding 3'UTR comprises a nucleotide sequence as shown in SEQ ID NO: 5.

In some embodiments, the replacement comprises using a Cas9-gRNA system.

In some embodiments, the gRNA is complementary to exon 4 of the mouse IL-15 gene.

In some embodiments, the gRNA is complementary to exon 8 of the mouse IL-15 gene.

In some embodiments, the gRNA complementary to exon 4 of the mouse IL-15 gene comprises a nucleotide sequence as shown in any one of SEQ ID NOs: 10-11.

In some embodiments, the gRNA complementary to exon 8 of the mouse IL-15 gene comprises a nucleotide sequence as shown in any one of SEQ ID NOs: 12-13.

In some embodiments, the gRNA complementary to exon 4 of the mouse IL-15 gene comprises a nucleotide sequence as shown in SEQ ID NO: 10; and the gRNA complementary to exon 8 of the mouse IL-15 gene comprises a nucleotide sequence as shown in SEQ ID NO: 13; or, the gRNA complementary to exon 4 of the mouse IL-15 gene comprises a nucleotide sequence as shown in SEQ ID NO: 11; and the gRNA complementary to exon 8 of the mouse IL-15 gene comprises a nucleotide sequence as shown in SEQ ID NO: 12.

In another aspect, the present application provides a use of the mouse in preparing a mouse model.

In some embodiments, the mouse model is used to evaluate the antagonistic effect of IL-15 antagonists on human IL-15-mediated functions in the mouse.

In some embodiments, the human IL-15-mediated functions comprise human IL-15-mediated lymphocyte development.

In some embodiments, the human IL-15-mediated functions comprise human IL-15-mediated lymphocyte infiltration of tissues or joints.

In some embodiments, the human IL-15-mediated functions comprise human IL-15-mediated inducible arthritis.

In some embodiments, the human IL-15-mediated functions comprise human IL-15-mediated NK cell development.

In some embodiments, the mouse model can be used to assess the antitumor efficacy of drugs. For example, the tumor comprises lymphocytic tumor. For example, the tumor comprises lung cancer.

Those skilled in the art can easily perceive other aspects and advantages of the present application from the detailed description below. In the following detailed description, only exemplary embodiments of the present application are shown and described. As those skilled in the art will recognize, the content of the present application enables those skilled in the art to make changes to the disclosed specific embodiments without departing from the spirit and scope of the invention involved in the present application. Correspondingly, the drawings and descriptions in the specification of the present application are merely exemplary, rather than restrictive.

BRIEF DESCRIPTION OF THE DRAWING

The specific features of the invention involved in the present application are shown in the appended claims. The characteristics and advantages of the invention involved in the present application can be better understood by referring to the exemplary embodiments and the accompanying drawings described in detail below. A brief description of the drawings is as follows:

FIGS. 5A and 5B respectively show the contents of human leukocytes and human NK cells in mice reconstituted with human peripheral blood NK cells, wherein FIG. 5A shows the hCD45+ proportion after transplantation, and FIG. 5B shows the hCD45+ hCD16+ proportion after transplantation.

FIGS. 6A and 6B show the flow cytometry results of human NK cells in mice reconstituted with human peripheral blood NK cells, wherein FIG. 6A shows the flow cytometry results of human peripheral blood NK cells, and FIG. 6B shows the flow cytometry results of NCG-IL15 humanized mouse.

FIG. 9 shows the reconstitution of humanized immune system in NCG-IL15 humanized mice after human HSC reconstitution, wherein FIG. 9A shows hCD45$^+$ proportion in peripheral blood after transplantation, FIG. 9B shows hCD3$^+$ cell proportion in peripheral blood hCD45$^+$ cell after transplantation, FIG. 9C shows hCD19$^+$ cell proportion in peripheral blood hCD45$^+$ cell after transplantation, FIG. 9D shows hCD4$^+$ cell proportion in peripheral blood hCD3$^+$ cell after transplantation, FIG. 9E shows hCD8$^+$ cell proportion in peripheral blood hCD3$^+$ cell after transplantation, and FIG. 9F shows hCD56$^+$ cell proportion in peripheral blood hCD45$^+$ cell after transplantation.

FIGS. 10A and 10B show the flow cytometry results of human NK cell functional proteins in human HSC-reconstituted 13-week-old mice, wherein FIG. 10A shows the flow cytometry results of NCG background mouse, and FIG. 10B shows the flow cytometry results of NCG-IL15 humanized mouse, in which the detection markers are CD16, CD56, KIR3DL, and NKG2D.

FIG. 12 shows the tumor cell killing effect and ADCC effect of human NK cells isolated from the spleen of NCG-IL15 humanized mice after HSC reconstitution, wherein FIG. 12A shows the cell killing ratio of NK cells, and FIG. 12B shows the cell killing ration of NK cells with Rituximab.

FIG. 13 shows the construction of an NCG-IL15 humanized mouse model after HSC reconstitution by subcutaneously inoculating human non-small cell lung cancer HCC827 cells as well as the profile of human immune cells in the peripheral blood and tumor tissues of the mice, wherein FIG. 13A shows the tumor volume after tumor cell inoculation, FIG. 13B shows the body weight of mice after tumor cell inoculation, and FIG. 13C, FIG. 13D and FIG. 13E show the flow cytometry results.

FIG. 14 shows the assessment on the anti-tumor effect of tumor immunotherapeutic antibodies in an NCG-IL15 humanized mouse model after HSC reconstitution and subcutaneously inoculating human lymphoma cells Raji, wherein FIG. 14A shows the tumor volume of mice after treatment, and FIG. 14B shows the body weight of mice after treatment.

DETAILED DESCRIPTION

Figure 1:
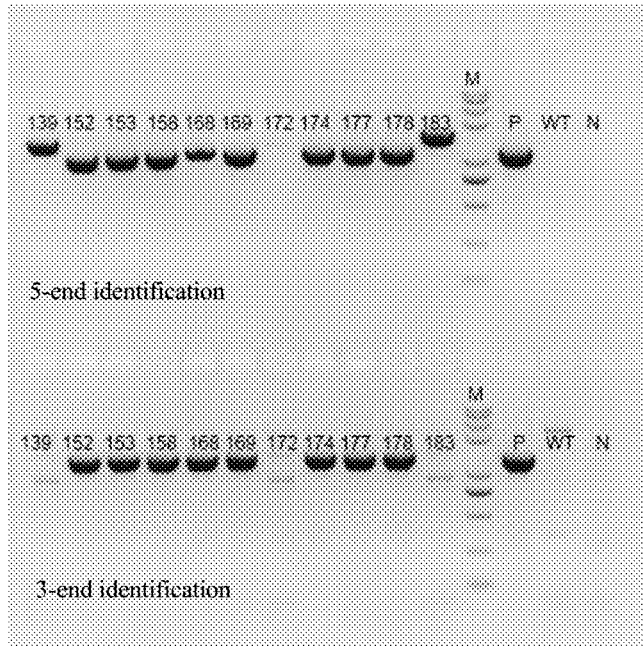
FIG. 1 shows an identification electropherogram of the 5' and 3' ends of F0 generation of mice.

The implementation of the present application will be illustrated in the following specific examples, and other advantages and effects of the present application will be easily known by those familiar with this technology from the content disclosed in the specification.

The following is a further description of the present application: In the present invention, unless otherwise specified, the scientific and technical terms used herein have the meanings commonly understood by those skilled in the art. In addition, protein and nucleic acid chemistry, molecular biology, cell and tissue culture, microbiology, immunology related terms and laboratory procedures used herein are all terms and routine procedures widely used in the corresponding fields. At the same time, in order to better understand the present invention, definitions and explanations of related terms are provided below.

In the present application, the term "functionally active part" generally refers to a partial structure that retains active functions. For example, a functionally active part of an organism, different from an intact organism, may be partial tissues or partial organs, but having essentially the same function and/or activity of the intact organism from which the functionally active part is derived. For example, the functionally active part of an organism may be blood, plasma, serum, urine, sweat, tear, saliva, semen and cerebrospinal fluid, skeleton, stomach, kidney, heart, liver, pancreas, lung, salivary gland or intestine.

In the present application, the term "IL-15", "IL15" and "interleukin 15" can be can be used herein interchangeably, and includes any variants or isotypes thereof naturally expressed by the cells. Interleukin 15 is a pro-inflammatory cytokine that acts as a potent growth, survival, and activation factor for T cells (especially intestinal intraepithelial lymphocytes (IEL)) and natural killer (NK) cells. Increased expression of IL-15 has been demonstrated in a variety of inflammatory disorders, including CD, rheumatoid arthritis (RA) and psoriasis (Malamut et, al., 2010). IL-15 is considered as the central regulator in the immunopathology of CD and the non-redundant driver of lymphoma formation in RCD. The inhibition of antagonists to IL-15 is an attractive therapeutic target for the treatment of CD. Targeting IL-15 by a fully human monoclonal antibody for binding IL-15 helps to elucidate the signaling mechanism promoted by IL-15 in CD, and an experimental proof-of-principle for the advantages of regulating downstream effectors of IL-15 has been established (Malamut et, al., 2010).

In the present application, the terms "sgRNA", "guide RNA", "single guide RNA" and "synthetic guide RNA" are interchangeable, and generally refers to a polynucleotide sequence containing a guide sequence. The guide sequence is about 20 bp, and within the guide RNA at the specified target site.

In the present application, the term "CRISPR" generally refers to clustered regularly interspaced short palindromic repeats. CRISPR locus generally differs from other SSRs in the structure of the repeats, which are called short regularly spaced repeats (SRSR). In general, repeats are short elements that occur in regularly interspaced clusters, with unique insertions of substantially constant length. The repeats are highly conserved between strains, but the number of interspersed repeats and the sequence of the spacers usually vary from strain to strain.

In the present application, the term "homologous recombination" generally refers to a type of genetic recombination, in which nucleotide sequences are exchanged between two similar or same DNA molecules that are called homologous sequences or homologous arms.

In the present application, the term "CRISPR-associated protein 9" or "Cas9 protein" generally refers to an RNA-guided DNA endonuclease that is associated with the type II CRISPR (regularly interspaced short palindromic repeats) adaptive immune system found in some bacteria, e.g., *Streptococcus pyogenes* or other bacteria. For example, Cas9 protein may not only include wild-type Cas9 found in *Streptococcus pyogenes*, but also include various variants thereof, such as those described in WO2013/176772A1. In some embodiments, as described in Esvelt et, al., Nature Methods, 10 (11): 1116-1121, 2013, Cas9 protein may include Cas9 sequence coming from *Streptococcus pyogenes, Neisseria meningitidis, Streptococcus thermophilus* and Dendritic nematodes.

In the present application, the term "Cas9 coding sequence" generally refers to a polynucleotide sequence capable of being transcribed and/or translated to produce Cas9 protein according to a genetic code that functions in the host cells/host animals. The Cas9 coding sequence may be DNA (e.g., plasmid) or RNA (e.g., mRNA).

In the present application, the term "Cas9 nucleoglucoprotein" generally refers to a protein/RNA complex composed of Cas9 proteins and associated guide RNAs.

In the present application, the term "CRISPR/Cas9 system" can also be called as "Cas9-gRNA system", which generally refers to a tool for site-specific genomic targeting in an organism. For example, it may be a type II CRISPR/

Cas system, a prokaryotic adaptive immune response system, which uses non-coding RNA to guide Cas9 nuclease to induce site-specific DNA cleavage. Such a DNA damage can be repaired through cellular DNA repair mechanism, via non-homologous end joining DNA repair pathway (NHEJ) or homology-directed repair (HDR) pathway. The CRISPR/Cas9 system can be utilized to establish a simple RNA programmable method to mediate the genome editing in mammalian cells, and to generate gene knockouts (via insertions/deletions) or knock ins (via HDR).

In the present application, the term "knock in" generally refers to a genetic engineering process which involves one-to-one replacement of DNA sequence information in a gene sequence or insertion of sequence information that is not found in an endogenous locus. Knock ins may involve the insertion of a gene of a particular locus, so it may be a "targeted" insertion.

In the present application, the term "targeting vector" generally refers to a vector carrying a targeting sequence to be inserted or incorporated into a host genome and/or for replacement of an endogenous DNA fragment.

In the present application, the term "embryonic stem cells" or "ES cells" generally refers to multipotent stem cells derived from the inner cell mass (ICM) of blastocyst (early preimplantation embryo of mammals), which can be cultured after prolonged in vitro culture, then inserted/injected into the normal blastocyst cavity and induced to resume normal embryonic developmental program so as to differentiate into various cell types of adult mammals, including germ cells.

In the present application, the term "zygote" generally refers to a eukaryotic cell formed by a fertilization event between two gametes, such as an egg and a sperm from a mammal.

In the present application, the term "zygosity" generally refers to the allelic similarity of traits in an organism.

In the present application, the term "homozygote" is used with regard to a particular gene or DNA (e.g., a heterologous nucleic acid sequence that has been knocked-in), and refers to diploid cells or organisms. The two homologous chromosomes both have the same alleles or gene/DNA copies.

In the present application, the term "heterozygote" is used with regard to a particular gene or DNA (e.g., a heterologous nucleic acid sequence that has been knocked-in), and refers to diploid cells or organisms. The two homologous chromosomes have different genes or DNA alleles/copies/versions.

In the present application, the term "IL-15 antagonists" generally refers to molecules that reduce, block, inhibit, abrogate, or interfere with signal transduction resulting from the interaction between IL-15 and one or more of its binding partners. Examples of the types of IL-15 antagonists may include molecules that bind to IL-15 family cytokines and inhibit their interaction with IL-15 receptors, for example, antibodies that specifically bind to IL-15 family cytokines, soluble polypeptides containing at least one exon of IL-15 receptors, and/or molecules that bind to IL-15 receptors and inhibit their interaction with IL-15 family cytokines (e.g., antibodies that specifically bind to IL-15 receptors). In some embodiments, IL-15 antagonists modulate, block, inhibit, reduce, antagonize, neutralize, or otherwise interfere with the biological activity of IL-15 cytokines. In some embodiments, IL-15 antagonists modulate, block, inhibit, reduce, antagonize, neutralize, or otherwise interfere with the biological activity of IL-15 receptors. In some embodiments, IL-15 antagonists may include small molecules.

In the present application, the term "human IL-15-mediated functions" generally refers to any lesions caused (alone or in association with other mediators), exacerbated, associated, or prolonged by abnormal human IL-15 levels in subjects with the disorder. In some examples, the human IL-15-mediated function may be lymphocyte dysplasia, for example, lymphocyte infiltration of tissues or joints or inducible arthritis.

In the present application, the term "human IL-15-mediated NK cell development" generally refers to that human IL-15 can induce and support the development of NK cells. In some instances, NK cells developed under the mediation of human IL-15 can express functional proteins. In some instances, NK cells developed under the mediation of human IL-15 can mediate ADCC effects and kill tumor cells. In some instances, NK cells developed under the mediation of human IL-15, as members of the innate immune system, can kill pathogens that invade the body.

In the present application, the term "comprising" generally refers to the inclusion of explicitly specified features, but not excluding other elements.

In the present application, the term "about" generally refers to varying within a range of 0.5%-10% above or below the specified value, for example, varying within a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below the specified value.

Mouse or Functionally Active Part Thereof

In one aspect, the present application provides a mouse or a functionally active part thereof, comprising a humanized IL-15 gene, wherein the humanized IL-15 gene comprises a human IL-15 gene segment and a mouse IL-15 gene segment, wherein the human IL-15 gene segment comprises at least a part of exon 4, exon 5, exon 6, exon 7, and exon 8 of the human IL-15 gene, wherein the mouse IL-15 gene segment comprises exon 1, exon 2 and exon 3 of the mouse IL-15 gene.

For example, the mouse or the functionally active part thereof comprises a humanized IL-15 gene, the humanized IL-15 gene comprises a human IL-15 gene segment and a mouse IL-15 gene segment, wherein the human IL-15 gene segment may include a part of exon 4, exon 5, exon 6, exon 7, and a part of exon 8 of the human IL-15 gene, the mouse IL-15 gene segment may include exon 1, exon 2 and exon 3 of the mouse IL-15 gene.

The functionally active part refers to a partial structure that retains active functions. For example, a functionally active part of an organism, different from an intact organism, may be partial tissues or partial organs, but having essentially the same function and/or activity of the intact organism from which the functionally active part is derived. For example, the functionally active part of an organism may be blood, plasma, serum, urine, sweat, tear, saliva, semen and cerebrospinal fluid, skeleton, stomach, kidney, heart, liver, pancreas, lung, salivary gland, or intestine. For another example, the functionally active part of the mouse may be blood, plasma, serum, urine, sweat, tear, saliva, semen and cerebrospinal fluid, skeleton, stomach, kidney, heart, liver, pancreas, lung, salivary gland, or intestine of the mouse.

In the present application, the exons in the human IL-15 gene segment may be composed of at least a part of exon 4, exon 5, exon 6, exon 7 and exon 8 of the human IL-15 gene.

For example, the exons in the human IL-15 gene segment may be composed of a part of exon 4, exon 5, exon 6, exon 7 and a part of exon 8 of the human IL-15 gene.

In some embodiments, the humanized IL-15 gene may include at least a part of exon 4, exon 5, exon 6, exon 7 and exon 8 of the human IL-15 gene.

For example, the humanized IL-15 gene may include a part of exon 4, exon 5, exon 6, exon 7 and a part of exon 8 of the human IL-15 gene.

In the present application, the human IL-15 gene segment may include a nucleic acid sequence as shown in SEQ ID NO: 1. The protein encoded by the human IL-15 gene segment may include an amino acid sequence as shown in SEQ ID NO: 7.

In the present application, the mouse IL-15 gene segment may also include a regulatory sequence of the mouse IL-15 gene. In some instances, the regulatory sequence may include a nucleotide sequence encoding a signal peptide of the mouse IL-15, a nucleotide sequence encoding 5'UTR and/or a nucleotide sequence encoding 3'UTR.

In the present application, the mouse IL-15 gene segment may include a nucleotide sequence encoding a signal peptide of the mouse IL-15. The nucleotide sequence encoding a signal peptide of the mouse IL-15 may include a nucleotide sequence as shown in SEQ ID NO: 3.

In the present application, the mouse IL-15 gene segment may include a nucleotide sequence encoding 5'UTR. The nucleotide sequence encoding 5'UTR may include a nucleotide sequence as shown in SEQ ID NO: 4.

In the present application, the mouse IL-15 gene segment may include a nucleotide sequence encoding 3'UTR. The nucleotide sequence encoding 3'UTR may include a nucleotide sequence as shown in SEQ ID NO: 5.

In some embodiments, the humanized IL-15 gene may include a nucleotide sequence encoding a signal peptide of the mouse IL-15. The nucleotide sequence encoding a signal peptide of the mouse IL-15 may include a nucleotide sequence as shown in SEQ ID NO: 3.

In some embodiments, the humanized IL-15 gene may include a nucleotide sequence encoding 5'UTR. The nucleotide sequence encoding 5'UTR may include a nucleotide sequence as shown in SEQ ID NO: 4.

In some embodiments, the humanized IL-15 gene may include a nucleotide sequence encoding 3'UTR. The nucleotide sequence encoding 3'UTR may include a nucleotide sequence as shown in SEQ ID NO: 5.

In the present application, the mouse IL-15 gene segment may not include at least a part of exon 4, exon 5, exon 6, exon 7 and exon 8 of the mouse IL-15 gene.

For example, the mouse IL-15 gene segment may not include a part of exon 4, exon 5, exon 6, exon 7 and a part of exon 8 of the mouse IL-15 gene.

In some embodiments, the humanized IL-15 gene may lack at least a part of exon 4, exon 5, exon 6, exon 7 and exon 8 of the mouse IL-15 gene.

For example, the humanized IL-15 gene may lack a part of exon 4, exon 5, exon 6, exon 7 and a part of exon 8 of the mouse IL-15 gene.

In the present application, the mouse may be an NCG mouse. The NCG mouse is a kind of severely immunodeficient mice that are deficient in T cells, B cells, and NK cells.

In some embodiments, the humanized IL-15 gene may include a nucleic acid sequence as shown in SEQ ID NO: 2. The protein encoded by the humanized IL-15 gene may include an amino acid sequence as shown in SEQ ID NO: 8.

In the present application, the IL-15 gene of the wild-type mouse (i.e., IL-15 is not humanized) may include a nucleotide sequence as shown in SEQ ID NO: 6. The IL-15 protein of the wild-type mouse (i.e., IL-15 is not humanized) may include an amino acid sequence as shown in SEQ ID NO: 9.

Offspring, Cell Line, Tissue, and Cell

In another aspect, the present application provides an offspring of the mouse or a functionally active part thereof, wherein the offspring or the functionally active part thereof comprises a humanized IL-15 gene, the humanized IL-15 gene comprises a human IL-15 gene segment and a mouse IL-15 gene segment, the human IL-15 gene segment comprises at least a part of exon 4, exon 5, exon 6, exon 7, and exon 8 of the human IL-15 gene, the mouse IL-15 gene segment comprises exon 1, exon 2 and exon 3 of the mouse IL-15 gene.

The offspring can be obtained by crossing the mouse of the present invention with a second mouse, wherein the second mouse may include or may not include the humanized IL-15 gene of the present application. For example, the offspring can be obtained by crossing the mouse of the present application with another mouse carrying not the same or different genetic information.

In another aspect, the present application provides a cell line or a primary cell culture, which is derived from the mouse or the functionally active part thereof; or derived from the offspring of the mouse.

In another aspect, the present application provides a tissue, which is derived from the mouse or the functionally active part thereof; or derived from the offspring of the mouse. In some embodiments, the tissue may include body fluid of the mouse or the offspring of the mouse. The body fluid may be selected from a group consisting of: blood, plasma, serum, urine, sweat, tear, saliva, semen, and cerebrospinal fluid.

In some embodiments, the tissue may be selected from a group consisting of: epithelial tissue, connective tissue, nerve tissue and muscle tissue.

In another aspect, the present application provides a cell, which is derived from the mouse or the functionally active part thereof; or derived from the offspring of the mouse. In some embodiments, the cell may be selected from a group consisting of: epithelial cells, nerve cells, erythrocytes, leukocytes, platelets, phagocytes, B lymphocytes, effector B cells, memory B cells, T lymphocytes, memory T cells, effector T cells, NK cells, dendritic cells, granulocytes, hemocytes, myocardial cells, smooth muscle cells, skeletal muscle cells, myocardial cells, osteoblasts, neurogliocytes, liver cells, renal cells, gland cells and endocrine cells.

In some embodiments, the cell cannot develop into an intact mouse. For example, the cell may not be totipotent stem cells or embryonic stem cells.

In some embodiments, the tissue or cell can be directly obtained from the mouse of the present application or the functionally active part thereof. Alternatively, the tissue or cell can be produced by introducing the humanized IL-15 gene sequence into its genome and optionally further culturing these modified cells/tissues.

Preparation Method

In another aspect, the present application provides a method for preparing a genetically modified mouse, the method includes:

replacing a mouse IL-15 gene segment encoding a mature mouse IL-15 polypeptide on an endogenous mouse IL-15 locus with a human IL-15 gene segment encoding a mature human IL-15 polypeptide so as to form a humanized IL-15 gene, wherein the human IL-15 gene segment comprises at least a part of exon 4, exon 5, exon 6, exon 7, and exon 8 of the human IL-15 gene.

For example, the method for preparing the genetically modified mouse of the present application may include: knocking in a human IL-15 gene segment encoding a mature human IL-15 polypeptide to an endogenous mouse IL-15 locus, to replace a mouse IL-15 gene segment encoding a mature mouse IL-15 polypeptide on the endogenous mouse IL-15 locus, so as to form a humanized IL-15 gene, wherein the human IL-15 gene segment may include at least a part of exon 4, exon 5, exon 6, exon 7, and exon 8 of the human IL-15 gene. The replaced mouse IL-15 gene segment may include at least a part of exon 4, exon 5, exon 6, exon 7, and exon 8 of the mouse IL-15 gene.

For example, in the coding region of the mouse, at least a part of exon 4, exon 5, exon 6 and exon 7, and exon 8 of the mouse IL-15 gene can be replaced with the human IL-15 gene segment, so as to form a humanized IL-15 gene, the coding region is a nucleic acid sequence that can be translated to produce a protein.

For another example, in the coding region of the mouse, a part of exon 4, exon 5, exon 6 and exon 7, and a part of exon 8 of the mouse IL-15 gene can be replaced with the human IL-15 gene segment, so as to form a humanized IL-15 gene, the coding region is a nucleic acid sequence that can be translated to produce a protein.

In the present application, the mouse IL-15 gene segment may include exon 1, exon 2 and exon 3 of the mouse IL-15 gene, and the exon 1, exon 2 and exon 3 of the mouse IL-15 gene are not replaced.

In the present application, the mouse IL-15 gene segment may also include a regulatory sequence of the mouse IL-15 gene. In some instances, the regulatory sequence may include a nucleotide sequence encoding a signal peptide of the mouse IL-15, a nucleotide sequence encoding 5'UTR and/or a nucleotide sequence encoding 3'UTR.

In the present application, the mouse IL-15 gene segment may include a nucleotide sequence encoding a signal peptide of the mouse IL-15. The nucleotide sequence encoding a signal peptide of the mouse IL-15 may include a nucleotide sequence as shown in SEQ ID NO: 3.

In the present application, the mouse IL-15 gene segment may include a nucleotide sequence encoding 5'UTR. The nucleotide sequence encoding 5'UTR may include a nucleotide sequence as shown in SEQ ID NO: 4.

In the present application, the mouse IL-15 gene segment may include a nucleotide sequence encoding 3'UTR. The nucleotide sequence encoding 3'UTR may include a nucleotide sequence as shown in SEQ ID NO: 5.

In some embodiments, the humanized IL-15 gene may include a nucleic acid sequence as shown in SEQ ID NO: 2. The protein encoded by the humanized IL-15 gene may include an amino acid sequence as shown in SEQ ID NO: 8.

In the present application, the mouse may be an NCG mouse.

In some embodiments, the exons in the human IL-15 gene segment may be composed of at least a part of exon 4, exon 5, exon 6, exon 7 and exon 8 of the human IL-15 gene.

For example, the exons in the human IL-15 gene segment may be composed of a part of exon 4, exon 5, exon 6, exon 7 and a part of exon 8 of the human IL-15 gene.

In the present application, the human IL-15 gene segment may include a nucleic acid sequence as shown in SEQ ID NO: 1.

In the present application, the replacement may include using a Cas9-gRNA system. The "Cas9-gRNA system" can also be called as "CRISPR/Cas9 system", which is a tool for site-specific genomic targeting in an organism. For example, it may be a type II CRISPR/Cas system, a prokaryotic adaptive immune response system, which uses non-coding RNA to guide Cas9 nuclease to induce site-specific DNA cleavage. Such a DNA damage can be repaired through cellular DNA repair mechanism, via non-homologous end joining DNA repair pathway (NHEJ) or homology-directed repair (HDR) pathway. The CRISPR/Cas9 system can be utilized to establish a simple RNA programmable method to mediate the genome editing in mammalian cells, and to generate gene knockouts (via insertions/deletions) or knock ins (via HDR).

In the present application, the gRNA may be complementary to exon 4 of the mouse IL-15 gene. In some instances, the gRNA complementary to exon 4 of the mouse IL-15 gene may include a nucleotide sequence as shown in any one of SEQ ID NOs: 10-11.

In the present application, the gRNA may be complementary to exon 8 of the mouse IL-15 gene. In some instances, the gRNA complementary to exon 8 of the mouse IL-15 gene may include a nucleotide sequence as shown in any one of SEQ ID NOs: 12-13.

In some instances, the gRNA complementary to exon 4 of the mouse IL-15 gene may include a nucleotide sequence as shown in SEQ ID NO: 10; and the gRNA complementary to exon 8 of the mouse IL-15 gene may include a nucleotide sequence as shown in SEQ ID NO: 13; or, the gRNA complementary to exon 4 of the mouse IL-15 gene may include a nucleotide sequence as shown in SEQ ID NO: 11; and the gRNA complementary to exon 8 of the mouse IL-15 gene may include a nucleotide sequence as shown in SEQ ID NO: 12.

In some instances, the gRNA complementary to exon 4 of the mouse IL-15 gene may include a nucleotide sequence as shown in SEQ ID NO: 10; and the gRNA complementary to exon 8 of the mouse IL-15 gene may include a nucleotide sequence as shown in SEQ ID NO: 12; or, the gRNA complementary to exon 4 of the mouse IL-15 gene may include a nucleotide sequence as shown in SEQ ID NO: 11; and the gRNA complementary to exon 8 of the mouse IL-15 gene may include a nucleotide sequence as shown in SEQ ID NO: 13.

Use

In another aspect, the present application provides a use of the mouse in preparing a mouse model.

In the present application, the mouse model comprises a humanized IL-15 gene, wherein the humanized IL-15 gene comprises a human IL-15 gene segment and a mouse IL-15 gene segment, wherein the human IL-15 gene segment comprises at least a part of exon 4, exon 5, exon 6, exon 7, and exon 8 of the human IL-15 gene, wherein the mouse IL-15 gene segment comprises exon 1, exon 2 and exon 3 of the mouse IL-15 gene.

For example, the mouse model comprises a humanized IL-15 gene, the humanized IL-15 gene comprises a human IL-15 gene segment and a mouse IL-15 gene segment, wherein the human IL-15 gene segment may include a part of exon 4, exon 5, exon 6, exon 7, and a part of exon 8 of the human IL-15 gene, the mouse IL-15 gene segment may include exon 1, exon 2 and exon 3 of the mouse IL-15 gene.

In the present application, the exons in the human IL-15 gene segment may be composed of at least a part of exon 4, exon 5, exon 6, exon 7 and exon 8 of the human IL-15 gene.

For example, the exons in the human IL-15 gene segment may be composed of a part of exon 4, exon 5, exon 6, exon 7 and a part of exon 8 of the human IL-15 gene.

In some instances, the humanized IL-15 gene may include at least a part of exon 4, exon 5, exon 6, exon 7 and exon 8 of the human IL-15 gene.

For example, the humanized IL-15 gene may include a part of exon 4, exon 5, exon 6, exon 7 and a part of exon 8 of the human IL-15 gene.

In the present application, the human IL-15 gene segment may include a nucleic acid sequence as shown in SEQ ID NO: 1. The protein encoded by the human IL-15 gene segment may include an amino acid sequence as shown in SEQ ID NO: 7.

In the present application, the mouse IL-15 gene segment may also include a regulatory sequence of the mouse IL-15 gene. In some instances, the regulatory sequence may include a nucleotide sequence encoding a signal peptide of the mouse IL-15, a nucleotide sequence encoding 5'UTR and/or a nucleotide sequence encoding 3'UTR.

In the present application, the mouse IL-15 gene segment may include a nucleotide sequence encoding a signal peptide of the mouse IL-15. The nucleotide sequence encoding a signal peptide of the mouse IL-15 may include a nucleotide sequence as shown in SEQ ID NO: 3.

In the present application, the mouse IL-15 gene segment may include a nucleotide sequence encoding 5'UTR. The nucleotide sequence encoding 5'UTR may include a nucleotide sequence as shown in SEQ ID NO: 4.

In the present application, the mouse IL-15 gene segment may include a nucleotide sequence encoding 3'UTR. The nucleotide sequence encoding 3'UTR may include a nucleotide sequence as shown in SEQ ID NO: 5.

For example, the humanized IL-15 gene may include a nucleotide sequence encoding a signal peptide of the mouse IL-15. The nucleotide sequence encoding a signal peptide of the mouse IL-15 may include a nucleotide sequence as shown in SEQ ID NO: 3.

For example, the humanized IL-15 gene may include a nucleotide sequence encoding 5'UTR. The nucleotide sequence encoding 5'UTR may include a nucleotide sequence as shown in SEQ ID NO: 4.

For example, the humanized IL-15 gene may include a nucleotide sequence encoding 3'UTR. The nucleotide sequence encoding 3'UTR may include a nucleotide sequence as shown in SEQ ID NO: 5.

In the present application, the mouse IL-15 gene segment may not include at least a part of exon 4, exon 5, exon 6, exon 7 and exon 8 of the mouse IL-15 gene.

For example, the mouse IL-15 gene segment may not include a part of exon 4, exon 5, exon 6, exon 7 and a part of exon 8 of the mouse IL-15 gene.

For example, the humanized IL-15 gene may lack at least a part of exon 4, exon 5, exon 6, exon 7 and exon 8 of the mouse IL-15 gene.

For example, the humanized IL-15 gene may lack a part of exon 4, exon 5, exon 6, exon 7 and a part of exon 8 of the mouse IL-15 gene.

In the present application, the mouse model may be an NCG mouse. The NCG mouse is a kind of severely immunodeficient mice that are deficient in T cells, B cells, and NK cells.

In the present application, the humanized IL-15 gene may include a nucleic acid sequence as shown in SEQ ID NO: 2. The protein encoded by the humanized IL-15 gene may include an amino acid sequence as shown in SEQ ID NO: 8.

In the present application, the IL-15 gene of the wild-type mouse (i.e., IL-15 is not humanized) may include a nucleotide sequence as shown in SEQ ID NO: 6. The IL-15 protein of the wild-type mouse (i.e., IL-15 is not humanized) may include an amino acid sequence as shown in SEQ ID NO: 9.

In the present application, the mouse model may be used to evaluate the antagonistic effect of IL-15 antagonists on human IL-15-mediated functions in the mouse.

For example, the mouse model may be used to evaluate the antagonistic effect of IL-15 antagonists on human IL-15-mediated functions in the mouse.

In the present application, the mouse may be used to reconstitute human lymphocytes.

In the present application, the lymphocytes may be NK cells, T cells, B cells.

In the present application, the mouse can be used to assess the antitumor efficacy of drugs.

For example, the mouse can be used to assess the efficacy of drugs for treating human lymphoma.

For example, the mouse can be used to assess the efficacy of drugs for treating human lung cancer.

In the present application, the "IL-15 antagonists" generally refers to molecules that reduce, block, inhibit, abrogate, or interfere with signal transduction resulting from the interaction between IL-15 and one or more of its binding partners. Examples of the types of IL-15 antagonists may include molecules that bind to IL-15 family cytokines and inhibit their interaction with IL-15 receptors, for example, antibodies that specifically bind to IL-15 family cytokines, soluble polypeptides containing at least one exon of IL-15 receptors, and/or molecules that bind to IL-15 receptors and inhibit their interaction with IL-15 family cytokines (e.g., antibodies that specifically bind to IL-15 receptors). In some embodiments, IL-15 antagonists modulate, block, inhibit, reduce, antagonize, neutralize, or otherwise interfere with the biological activity of IL-15 cytokines. In some embodiments, IL-15 antagonists modulate, block, inhibit, reduce, antagonize, neutralize, or otherwise interfere with the biological activity of IL-15 receptors. In some embodiments, IL-15 antagonists may include small molecules.

In the present application, the "human IL-15-mediated functions" generally refers to any lesions caused (alone or in association with other mediators), exacerbated, associated, or prolonged by abnormal human IL-15 levels in subjects with the disorder. In some examples, the human IL-15-mediated function may be lymphocyte dysplasia, for example, lymphocyte infiltration of tissues or joints, inducible arthritis, or lymphocytic tumor (e.g., B cell tumor or T cell tumor).

For example, the human IL-15-mediated functions may include human IL-15-mediated lymphocyte development. In some embodiments, the human IL-15-mediated functions may include human IL-15-mediated lymphocyte infiltration of tissues or joints. In the present application, the human IL-15-mediated functions may include human IL-15-mediated inducible arthritis. In the present application, the human IL-15-mediated functions may include lymphocytic tumor, e.g., B cell tumor or T cell tumor. In the present application, the human IL-15-mediated functions may include rheumatoid arthritis. In the present application, the IL-15-mediated functions may include mediated NK cell development. For example, the NK cells can kill tumor cells.

Without wishing to be limited by any theory, the examples below are intended only to illustrate the mouse model, preparation method, uses, etc. of the present application, and are not intended to limit the inventive scope of the present application. The examples do not include detailed description of conventional methods, such as those for constructing vectors and plasmids, those for inserting genes encoding the protein into such vectors and plasmids or those for introducing plasmids into host cells. Such methods are well known to persons with ordinary skills in the art, and have been described in many publications, including Sambrook, J., Fritsch, E. F. and Maniais, T. (1989) Molecular Cloning: A Laboratory Manual, 2nd edition, Cold spring Harbor Laboratory Press.

EXAMPLES

Example 1. Preparation of the Mouse of the Present Application

By means of CRISPR/Cas9, part of exon 4 (Exon 4), exon 5 (Exon 5), exon 6 (Exon 6), exon 7 (Exon 7) and part of exon 8 (Exon 8) of the human IL-15 gene were fused, and part of exon 4 (Exon 4), exon 5 (Exon 5), exon 6 (Exon 6), exon 7 (Exon 7) and part of exon 8 (Exon 8) of the mouse IL-15 gene were then replaced with the fused gene to establish an IL-15 gene humanized mouse model (i.e, the mouse of the present application). It should be noted that, the mice used in the preparation were NCG mice (female mice of 8-week-old, male mice of 10-week-old, provided by GemPharmatech Co., Ltd.). The mouse of the present application were prepared specifically by the following steps:
1.1. Determination of Replacement Regions of Human Fragments and Inserted Human Sequence According to humanized IL-15 protein functional domains and human-mouse homology comparison, part of exon 4 (Exon 4), exon 5 (Exon 5), exon 6 (Exon 6), exon 7 (Exon 7), part of exon 8 (Exon 8) of the humanized IL-15 gene were selected and fused to replace part of exon 4 (Exon 4), exon 5 (Exon 5), exon 6 (Exon 6), exon 7 (Exon 7), part of exon 8 (Exon 8) of the mouse IL-15 gene, retaining part of the signal peptide and the whole UTR sequence of the mouse IL-15 gene. The sequence of the selected humanized IL-15 gene (i.e, the human IL-15 gene segment of the present application) was shown in SEQ ID No: 1, and the amino acid sequence of its coding region was shown in SEQ ID No: 7; before the mice were humanized, the sequence of its IL-15 gene was shown in SEQ ID No: 6, and its IL-15 amino acid sequence was shown in SEQ ID No: 9.
1.2. Screening of sgRNA Prepared for IL-15 Humanized Mice The approximate region of sgRNA was determined according to the human IL-15 gene segment, and several groups of sequence (Table 1-1) with the lowest off-target rate for the target fragment was selected as the sgRNA to be selected. 5'-end target site and 3'-end target site for recognition were designed and synthesized, and sgRNA expression vectors were constructed. The sgRNA recognition sites at both ends were located at the fourth and the eighth exons of the mouse IL-15 gene, respectively, and the target site sequence and the primer sequence of each sgRNA on IL-15 were shown in Table 1-1 and Table 1-2.

TABLE 1-1

| sgRNA sequence information | | | |
|---|---|---|---|
| sgRNA Name | sgRNA Sequence (5'→3') SEQ ID No: | | PAM Rule |
| IL15-5S1 | 10 | | GGG |
| IL15-5S2 | 11 | | TGG |
| IL15-3S1 | 12 | | TGG |
| IL15-3S2 | 13 | | AGG |

16

TABLE 1-2

| sgRNA primer information | |
|---|---|
| sgRNA Primer Name | sgRNA Primer Sequence (5'→3') SEQ ID No: |
| 710022-IL15-5S1F | 14 |
| 710022-IL15-5S1R | 15 |
| 710022-IL15-5S2F | 16 |
| 710022-IL15-5S2R | 17 |
| 710022-IL15-3S1F | 18 |
| 710022-IL15-3S1R | 19 |
| 710022-IL15-3S2F | 20 |
| 710022-IL15-3S2R | 21 | sgRNA transcription: PCR was performed with the PrimerStar Max system (for details, see Table 2-1 and Table 2-2), with sgRNA-F and sgRNA-R as primers (that is, with the sequences in Table 1-2 as the primer), and with the correctly sequenced puc57-sgRNA plasmid (purchased from NEB Co., Item No. R0535V, dilution at 1:30) as the template. PCR products were purified to prepare sgRNA transcription preparation template. The transcription of sgRNA was performed using a T7-ShortScript in vitro transcription kit (purchased from Invitrogen Co., AM1354).

TABLE 2-1

| PCR reaction system | | |
|---|---|---|
| Reagents (Takara R045) | Volume (µl) | Specification |
| 2 × Taq Master Mix (Dye Plus) | 12.5 | \ |
| ddH₂O | 9.5 | \ |
| Primer | 1 | 10 µM |
| Primer | 1 | 10 µM |
| Template | 1 | |

TABLE 2-2

| PCR reaction conditions Touchdown PCR program | | | | |
|---|---|---|---|---|
| Seg. | Temperature | Time | Cycles | ±Temperature/Cycles |
| 1 | 95° C. | 5 min | | |
| 2 | 98° C. | 30 s | | |
| 3 | 65° C. | 30 s | | −0.5 |
| 4 | 72° C. | 45 s | 2-4, 20× | |
| 5 | 98° C. | 30 s | | |
| 6 | 55° C. | 30 s | | |
| 7 | 72° C. | 45 s | 5-7, 20× | |
| 8 | 72° C. | 5 min | | |
| 9 | 10° C. | Keeping | | | sgRNA screening: The 5'-end target site and 3'-end target site sgRNAs were screened respectively and paired to form 2 pairs of sgRNAs, for details of each sgRNA combination, see Table 3. These sgRNAs and Cas9 proteins (purchased from Chinapeptides Co., Ltd.) were incubated respectively, and then the mixture was injected into fertilized eggs of 0.5-day-old mice (GemPharmatech Co., Ltd.), and cultured to the blastocyst stage. Then the KO positive rate of the mouse IL-15 gene was identified so as to screen sgRNA pairs.

Identification of sgRNA cleavage: The collected blastocysts were subjected to PCR amplification (PCR scheme was as below). Statistics was conducted based on the results of PCR (the target band can be amplified only when KO occurs), to get the probability of occurrence of KO (i.e., cleavage efficiency, with the identification results shown in Table 3). According to the location of each sgRNA and the cleavage efficiency of various combinations, the IL15-5S1+ IL15-3S2 combination was finally selected for subsequent experiments.

TABLE 3

| sgRNA cleavage activity | |
| --- | --- |
| Single-end sgRNA or various sgRNA combinations | Probability of occurrence of KO |
| IL15-5S1 | 18.2% |
| IL15-5S2 | 33.3% |
| IL15-3S1 | 75% |
| IL15-3S2 | 88% |
| IL15-5S1 + IL15-3S2 | 20% |
| IL15-5S2 + IL15-3S1 | 25% |

1.3. Construction of Humanized Targeting Carriers

Using a technique of homologous recombination, part of exon 4 (Exon 4), exon 5 (Exon 5), exon 6 (Exon6), exon 7 (Exon 7) and part of exon 8 (Exon 8) of the mouse IL-15 gene were replaced with the humanized IL-15 gene described above. The successfully-constructed targeting carriers have a sequence as shown in SEQ ID No: 2. The constructed targeting carriers were transcribed and then reverse transcribed to obtain ssDNA (single stranded) donors available for injection.

1.4. Establishment of IL-15 Humanized Mouse Model ssDNA (single stranded) donors and Cas9/sgRNA system (i.e., sgRNA containing Cas9 protein) were injected into fertilized eggs of 0.5-day-old mice (GemPharmatech Co., Ltd.), and then transplanted into 0.5-day-old pseudopregnant female mice (GemPharmatech Co., Ltd.). After birth, targeted mice were screened out through genetic identification. It should be noted that, the postnatal mice were collectively referred to as F0 generation of mice, where the targeted mice (i.e., containing the humanized IL-15 gene of the present application) were collectively referred to as positive F0 generation of mice.

Identification of F0 generation genotype of humanized mice: The mouse tail genomic DNA of the obtained F0 generation of mice was identified by PCR on both ends after targeting using two pairs of primers. The primers 710022-IL15-5tF1/710022-IL15-5tR1 were respectively located outside 5' homologous arm and inside the humanized fragment of the ssDNA (single stranded) donor; if a PCR product was produced after amplification by this pair of primers, it means that the target donor has been effectively inserted into the genome 5' of the mouse. 710022-IL15-3tF1/710022-IL15-3tR1 were respectively located inside the humanized fragment of the ssDNA (single stranded) donor and outside 3' homologous arm; if a PCR product was produced after amplification by this pair of primers, it means that the target donor has been effectively inserted into the genome 3' of the mouse. The primer sequences were specifically shown in Table 4, and the PCR reaction system and the reaction conditions were shown in Table 2-1 and Table 2-2.

TABLE 4

| Primers for genetic identification of FO generation of mice | |
| --- | --- |
| Primer Name | Primer Sequence (SEQ ID No:) |
| 710022-IL15-5tF1 | 22 |
| 710022-IL15-5tR1 | 23 |
| 710022-IL15-3tF1 | 24 |
| 710022-IL15-3tR1 | 25 |

Mouse clones identified by PCR as positive at both ends were verified by sequencing, with the sequencing primers specifically shown in Table 5. After sequencing, it was found that the amino acid sequence of the IL-15 protein of positive F0 generation of mice was shown in SEQ ID No: 8, and the nucleotide sequence encoding the IL-15 protein (i.e., the humanized IL-15 gene of the present application) was shown in SEQ ID No: 2.

TABLE 5

| Sequencing primers for mouse clones identified by PCR as positive at both ends | |
| --- | --- |
| Primer Name | Primer Sequence (SEQ ID No:) |
| 710022-IL15-5tF1 | 22 |
| 710022-IL15-5tR1 | 23 |
| 710022-IL15-3tF1 | 24 |
| 710022-IL15-3seqR1 | 26 |
| 710022-IL15-WT-TF1 | 27 |
| 710022-IL15-WT-TR1 | 28 |

Four positive F0 generation of mice were finally obtained. As shown in FIG. 1. WT in the figure indicates the genomic DNA of NCG mice without knock-out/knock-in (Negative control); N is the blank control (i.e, a control without template); P is the positive control (i.e, a targeting carrier); M is a marker: TRANS 2K PLUS II strip: 8000 bp\5000 bp\3000 bp\2000 bp\1000 bp\750 bp\500 bp\250 bp\100 bp), from which it shows that, the humanized IL-15 gene 5' and 3' of 152 #, 153 #, 158 #, 169 #, 174 #, 178 #mice were all identified as positive, and there was no mutation in the sequencing, indicating that these mice were positive F0 generation of mice with correct gene recombination.

Positive F0 generation of mice were bred with background mice (i.e., NCG mice without knock-out/knock-in) to obtain F1 generation of mice, the tails of which were genetically identified, and the targeted mice (i.e., containing the humanized IL-15 gene of the present application) were collectively referred to as positive F1 generation of mice. The sequencing primers were shown in Table 5, wherein primers 710022-IL15-WT-TF1 and 710022-IL15-WT-TRI were used to detect the genomic DNA of NCG mice without knock-out/knock-in. After sequencing, it was found that the amino acid sequence of the IL-15 protein of positive F1 generation of mice was shown in SEQ ID No: 8, and the nucleotide sequence encoding the IL-15 protein (i.e., the humanized IL-15 gene of the present application) was shown in SEQ ID No: 2.

Figure 2:
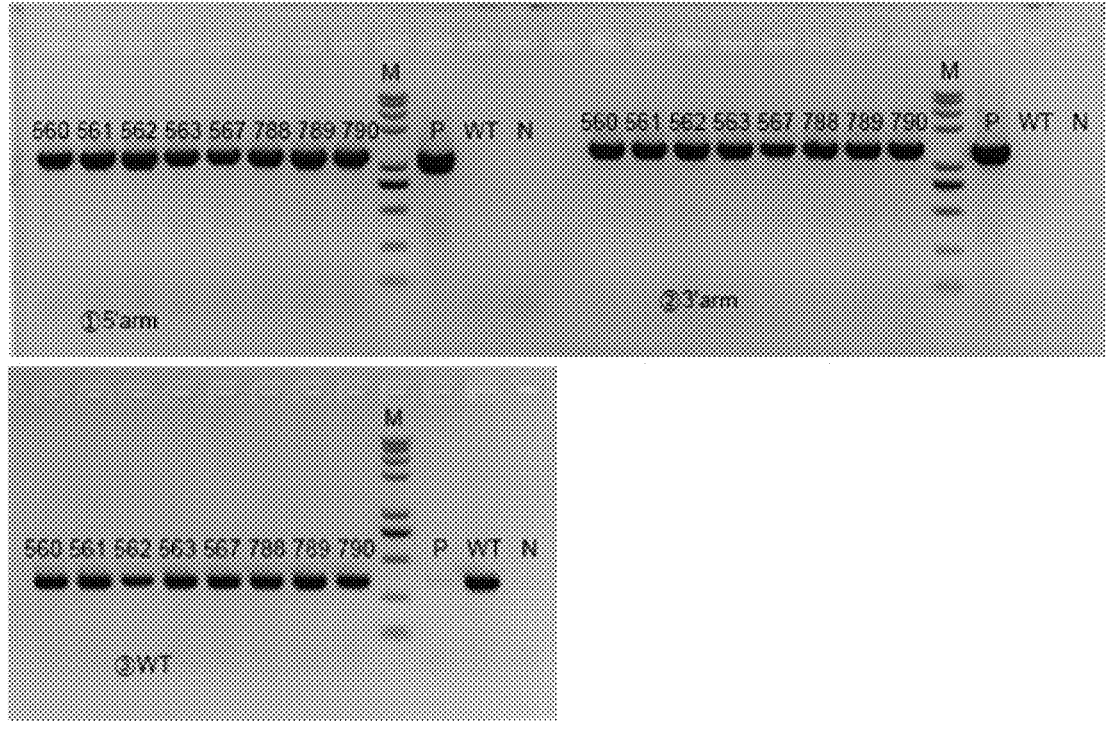
FIG. 2 shows an identification electropherogram of the 5' and 3' ends of F1 generation of mice.

The PCR experimental results of F1 generation of mice were shown in FIG. 2. WT in the figure indicates the genomic DNA of NCG mice without knock-out/knock-in (Negative control); N is the blank control (i.e, a control without template); P is the positive control (i.e, a targeting carrier); M is a marker: TRANS 2K PLUS II strip:

8000 bp\5000 bp\3000 bp\2000 bp\1000 bp\750 bp\500 bp\250 bp\100 bp), from which It shows that, the humanized IL-15 gene 5' and 3' of 560 #, 561 #, 562 #, 563 #, 567 #, 788 #, 789 #, 790 #mice were all identified as positive, and the detection of mouse origin was also positive, indicating that the obtained mice were heterozygous positive mice with correct gene recombination. The F1 generation mice were multiplied and bred to obtain homozygotes.

Example 2. Expression and Detection of Humanized IL-15 in NCG-IL15 Mice 2.1. Expression and Detection of Humanized IL-15 mRNA Heart, liver, spleen, lung, kidney, intestine, stomach, muscle, ovary, bone marrow, peripheral blood, and brain tissues of NCG background mice (i.e., NCG mice without knock-out/knock-in) and NCG-IL15 humanized mice (i.e., mice of the present application, progeny mice of the F1 generation of mice in Example 1, homozygotes) were selected, from which mRNA was extracted and reverse-transcripted to cDNA, and mRNA expression levels of murine IL-15 in NCG mice and humanized IL-15 in NCG-IL15 humanized mice were detected by Q-PCR, with the primers for detecting the expression specifically shown in Table 6.

TABLE 6

| Primers for detecting the expression of IL-15 | |
| --- | --- |
| Primer Name | Primer Sequence (SEQ ID No:) |
| mIL15-RT-qTF1 | 29 |
| mIL15-RT-qTR1 | 30 |
| hIL15-RT-qTF1 | 31 |
| hIL15-RT-qTR1 | 32 |

Figure 3:
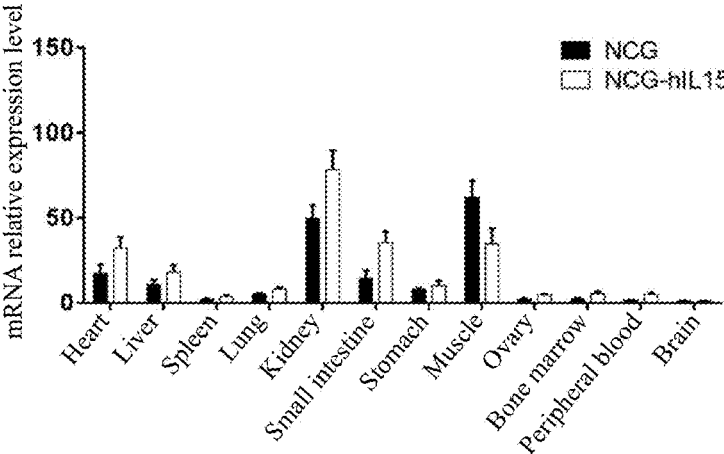
FIG. 3 shows mRNA expression of IL-15 in various tissues of NCG-IL15 humanized mice and NCG background mice.

The Q-PCR detection results were shown in FIG. 3. In this figure, NCG represents NCG background mice, NCG-hIL15 represents NCG-IL15 humanized mice. It shows that, the expression levels of murine IL15 in heart, liver, kidney, small intestine and muscle tissues of background mice were higher, and the expression levels in spleen, lung, stomach, ovary, bone marrow, peripheral blood and brain tissues were lower; However, the tissue expression specificity of humanized IL15 in NCG-IL15 humanized mice was consistent with that in NCG background mice, the expression levels in heart, liver, kidney, small intestine and muscle tissues were higher, and the expression levels in spleen, lung, stomach, ovary, bone marrow, peripheral blood and brain tissues were lower.

2.2. Detection of Protein Expression

Peripheral blood of NCG background mice (i.e., NCG mice without knock-out/knock-in) and NCG-IL15 humanized mice (i.e., mice of the present application, progeny mice of the F1 generation of mice in Example 1, heterozygote NCG-hIL15h/m and homozygote NCG-hIL15h/h) were selected, for which a humanized IL-15 Elisa detection kit (purchased from R&D Co., Item No. D1500) was used to detect the expression of human IL-15 protein in the sera.

Figure 4:
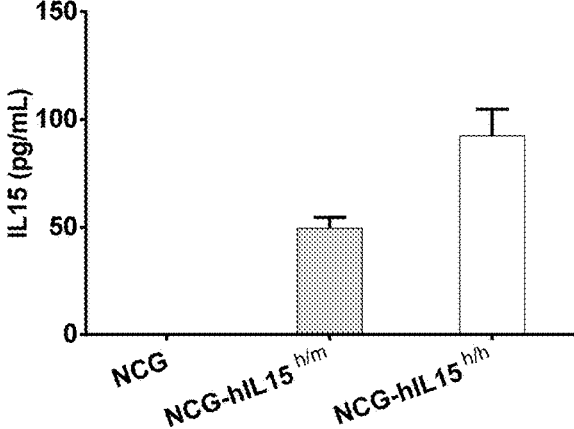
FIG. 4 shows IL-15 protein level in peripheral sera of NCG-IL15 humanized mice and NCG background mice.

The results were shown in FIG. 4. In the figure, NCG-hIL15 represents NCG-IL15 humanized mice. It shows that, the expression of humanized IL15 was not detected in background mice, while the expression of humanized IL15 was detected in both heterozygotes and homozygotes of NCG-IL15 humanized mice, and the expression levels in homozygotes were higher than those in heterozygotes.

Example 3. Detection on the Development of Humanized NK Cells Transplanted into NCG-IL15 Mice NCG background mice (i.e., NCG mice without knock-out/knock-in) and NCG-IL15 humanized mice (i.e., mice of the present application, progeny mice of the positive F1 generation of mice in Example 1, which were heterozygotes) were selected. NK cells purified from human peripheral blood (huPBMC-NK, purchased from Miao Tong Biological Science & Technology Co., Ltd.) were injected into mice by means of tail vein injection. The development of human NK cells in peripheral blood was detected by flow cytometry (purchased from Thermo Attune NxT Co.).

Figure 5:
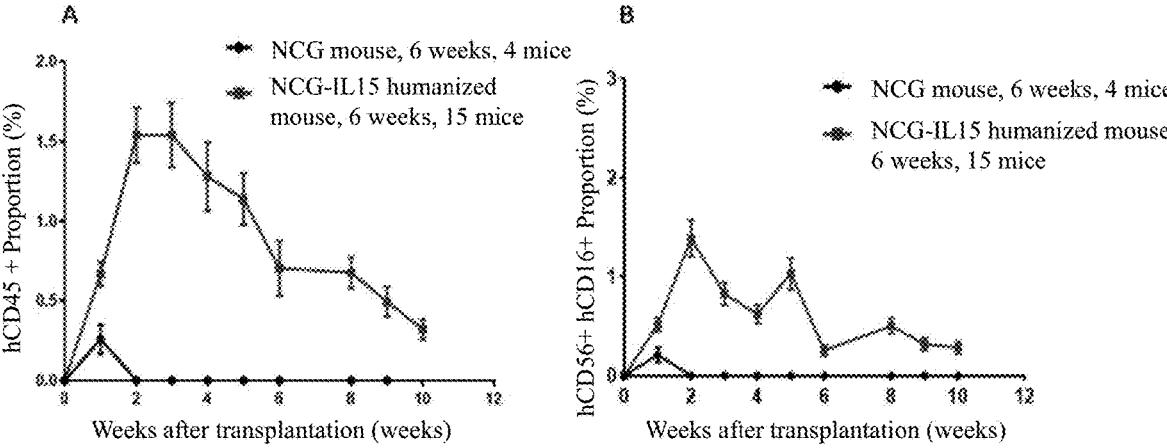

The results were shown in FIG. 5A and FIG. 5B. It shows that, in background mice the proportion of human leukocytes (detection Marker: hCD45) was low, the proportion of human NK cells (detection Marker: hCD56hCD16) was low and can only be maintained for about 2 weeks; while in NCG-IL15 humanized mice, the proportion of human leukocytes was higher than that in background mice, the human NK cells could maintain for up to 10 weeks, and the proportion was higher than that in NCG background mice.

Figure 6:
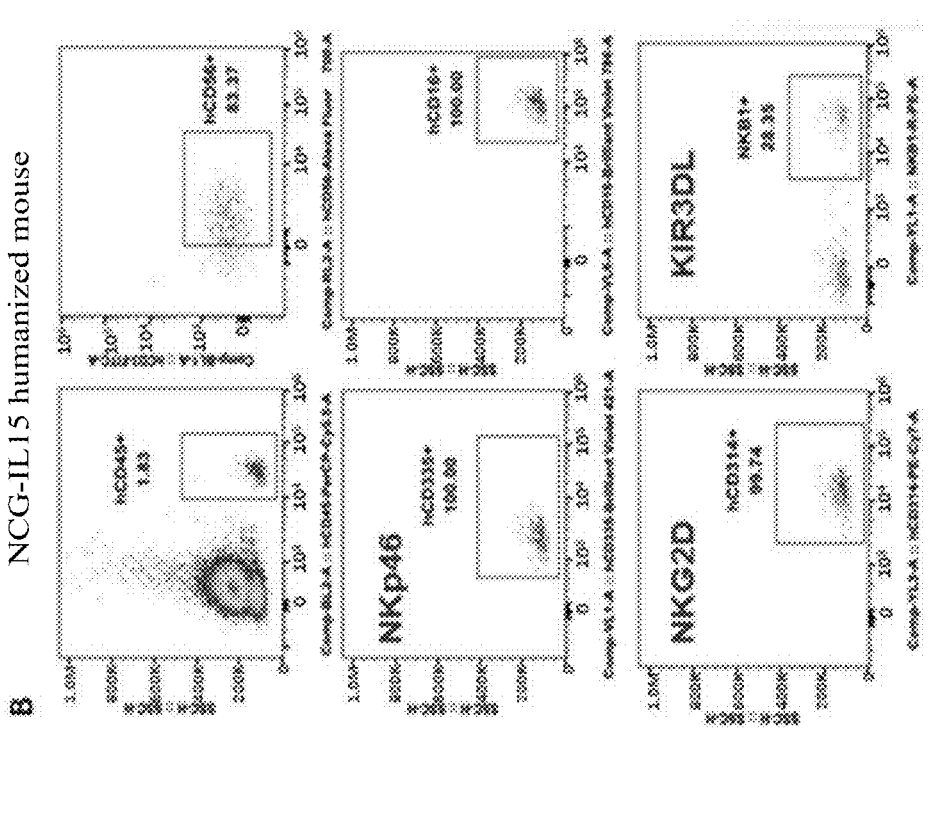
Figure 6:
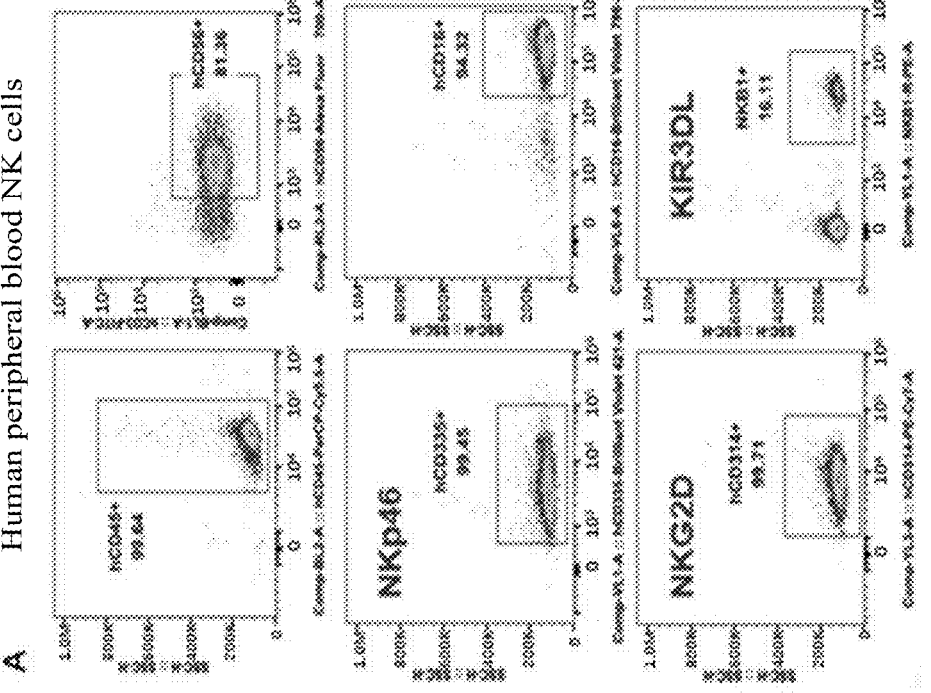
Figure 7:
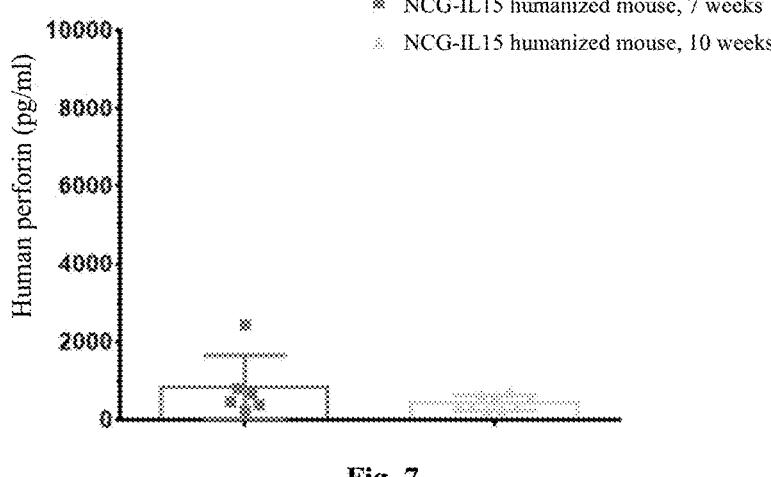
FIG. 7 shows the results of NCG-IL15 humanized mice reconstituted with human peripheral blood NK cells to secrete human perforin.

The functions of human NK cells reconstituted in NCG-IL15 humanized mice were detected, with the results shown in FIG. 6A and FIG. 6B. It shows that, the proportion of functional Marker of human NK reconstituted in NCG-IL15 humanized mice has no significant change compared with that before transplantation, and it can secrete perforin (as shown in FIG. 7), suggesting that human NK cells developed from NCG-IL15 humanized mice have normal physiological functions.

Example 4. Detection on the Immune Reconstitution Process of Transplanting Human Hematopoietic Stem Cells (HSCs) in NCG-IL15 Mice NCG background mice (i.e., NCG mice without knock-out/knock-in) and NCG-IL15 humanized mice (i.e., mice of the present application, progeny mice of the positive F1 generation of mice in Example 1, which were heterozygotes) were selected. Human CD34+ hematopoietic stem cells (HSCs) (huHSC, purchased from Miao Tong Biological Science & Technology Co., Ltd.) were injected into mice by means of tail vein injection. The survival and weight change of mice were monitored and the development of human immune cells in peripheral blood was detected by flow cytometry (purchased from Thermo Attune NxT Co.).

Figure 8:
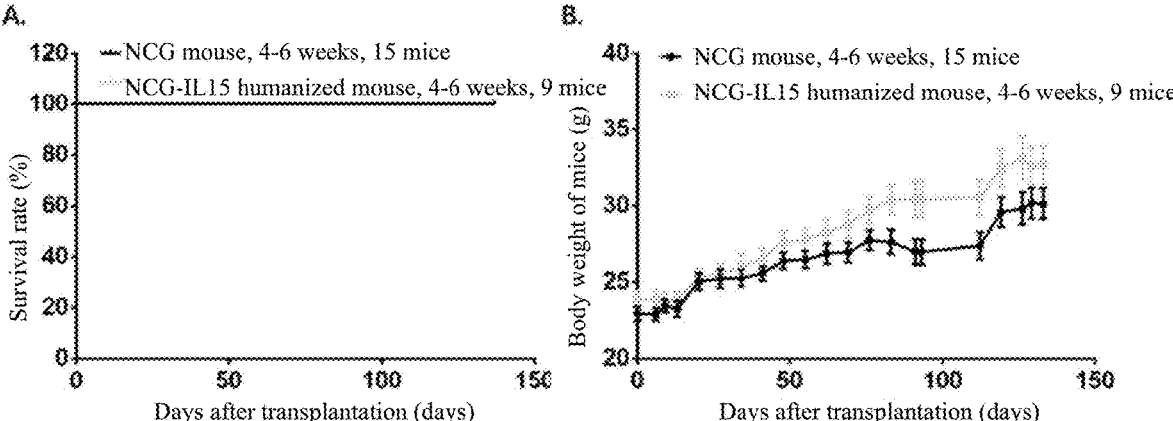
FIG. 8A and FIG. 8B show the survival and body weight changes of mice after human HSC reconstitution.
Figure 9:
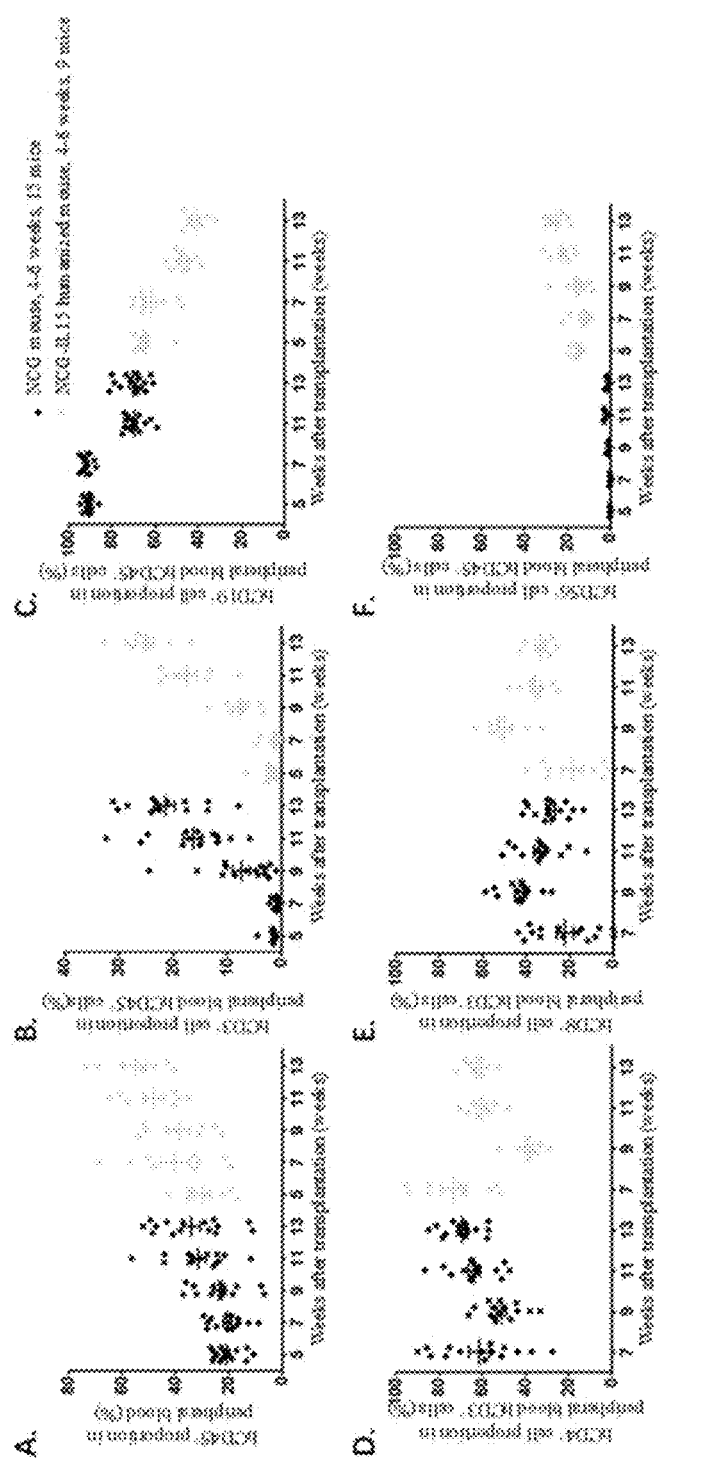

The survival and weight change of mice were shown in FIG. 8A and FIG. 8B. There was no mouse death within 18 weeks after transplantation of human hematopoietic stem cells (HSCs), meanwhile the body weight of mice showed a stable increasing trend. At the same time, peripheral blood was collected from NCG background mice and huHSC-NCG-hIL15 mice on weeks 5, 7, 9, 11, 13, and the immune reconstitution processes of NCG background mice and NCG-IL15 mice were detected by flow cytometry (purchased from Thermo Attune NxT Co.), for which the detection indicators were hCD45, hCD3, hCD19, hCD4, hCD8, hCD56. As shown in FIGS. 9A-9E, the level of hCD45+ leukocytes in the peripheral blood of NCG-IL15 mice after being injected with HSC cells has reached over 20% from week 5, and the reconstitution ratio was higher than that in NCG background mice; the level of hCD3+ T cells gradually increased from week 9, and differentiated into hCD4+ and hCD8+ T cell subsets. As shown in FIG. 9F, compared with that in NCG background mice, the level of hCD56+NK cell reconstitution in the peripheral blood hCD45+ of NCG-IL15 humanized mice was significantly increased (about 20%), suggesting that IL15 expressed in NCG-IL15 humanized mice supports the colonization and amplification of NK cells in mice.

Figure 10:
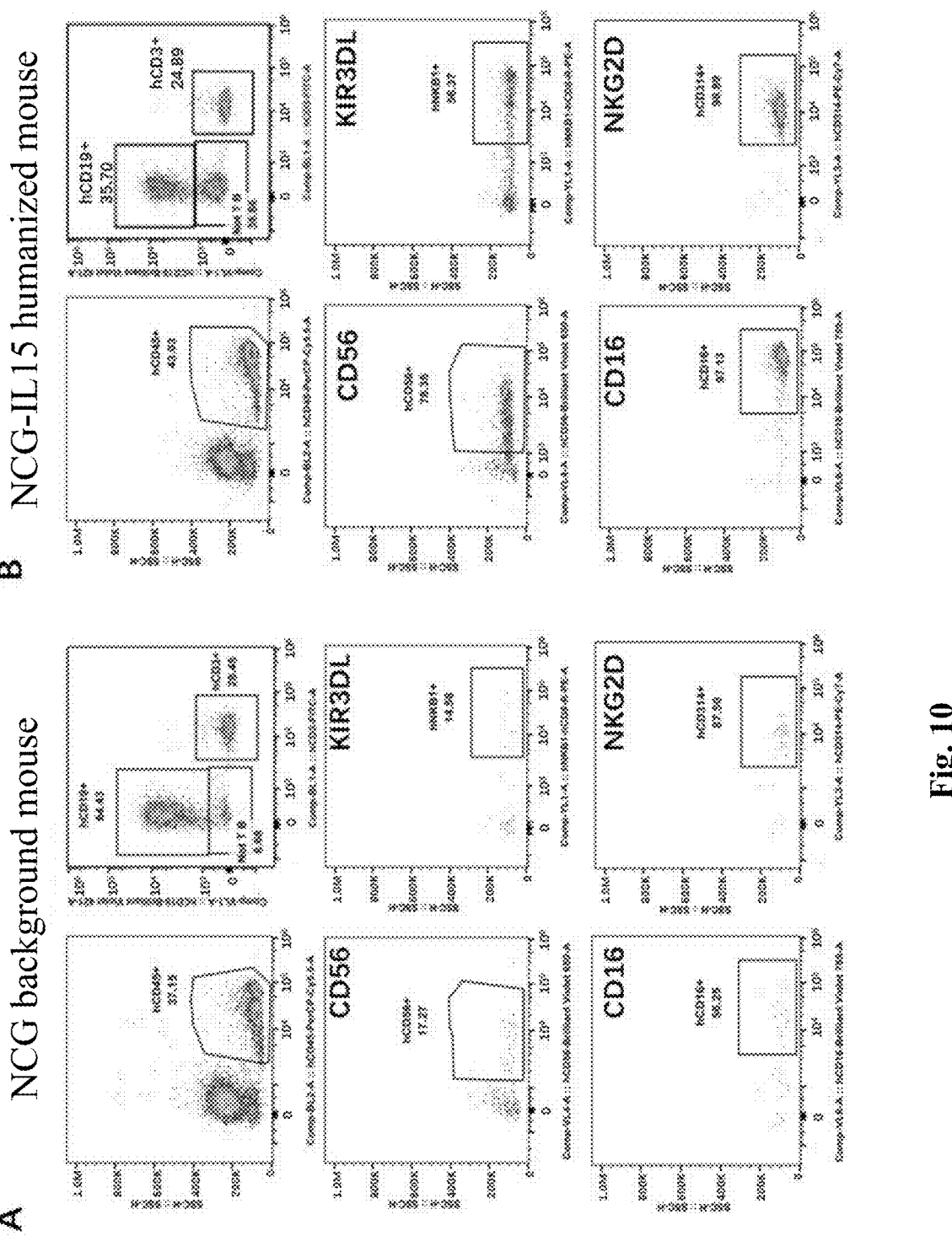
Figure 11:
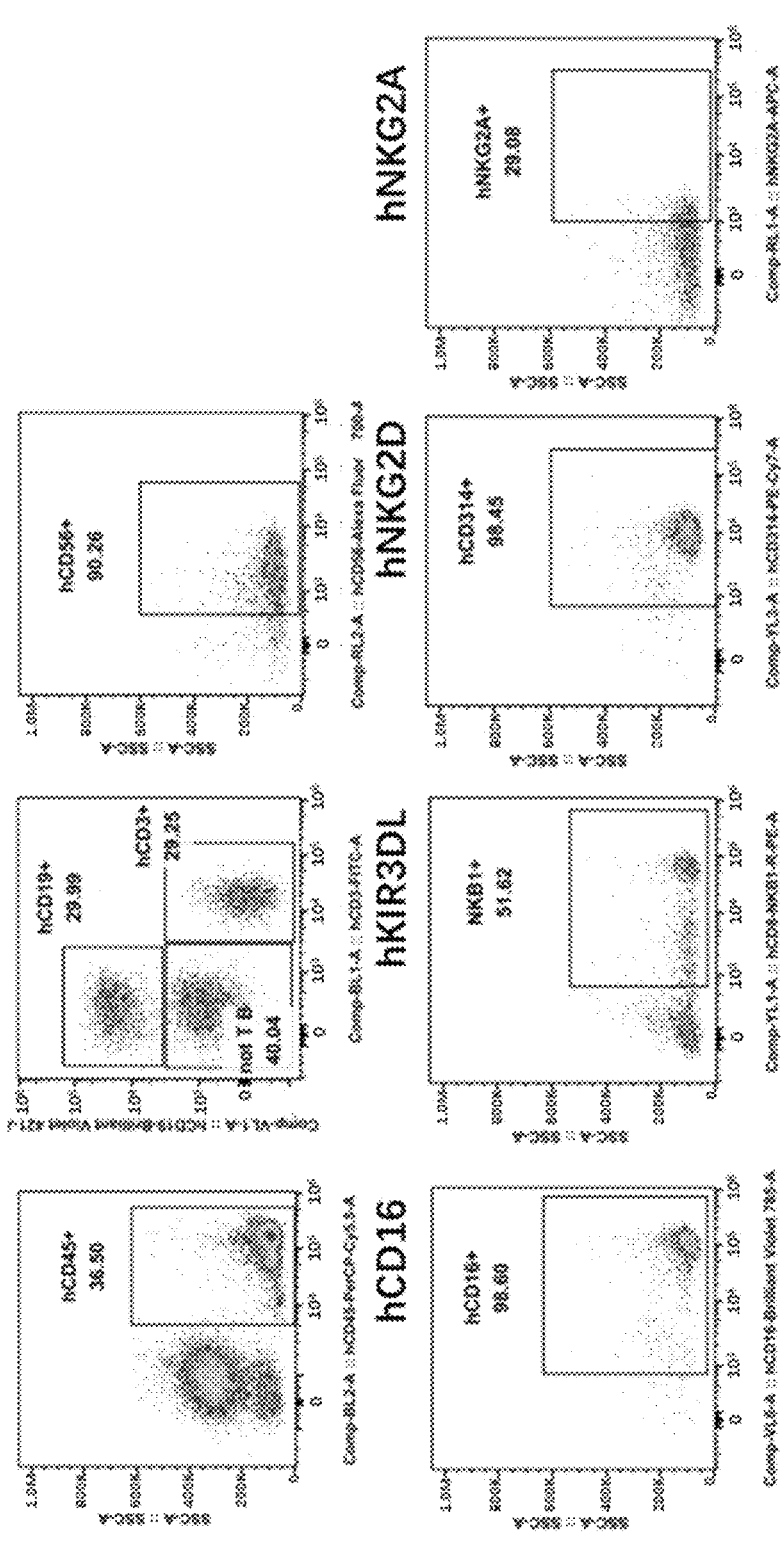
FIG. 11 shows the flow cytometry results of human NK cell functional proteins in human HSC-reconstituted 18-week-old NCG-IL15 humanized mice, in which the functional proteins are CD16, CD56, KIR3DL, and NKG2D.

The functions of human NK cells reconstituted after transplantation of hematopoietic stem cells (HSCs) in NCG-IL15 humanized mice were detected, with the results at week 13 after reconstitution shown in FIG. 10A and FIG. 10B, from which it shows the functional markers are expressed in human NK reconstituted in NCG-IL15 humanized mice (hCD16, hKIR3DL, hNKG2D). The results at week 18 after reconstitution were shown in FIG. 11, from which it shows functional markers are sustainably expressed in human NK reconstituted in NCG-IL15 humanized mice (hCD16, hKIR3DL, hNKG2D, hNKG2A), suggesting that human NK cells differentiated and amplified from hematopoietic stem cells in NCG-IL15 humanized mice have sustainable and normal physiological functions.

Example 5. Detection on the Killing and ADCC Effects of NK Cells Reconstituted after Transplantation of Human Hematopoietic Stem Cells (HSCs) in NCG-IL15 Mice NCG-IL15 humanized mice (i.e., mice of the present application, progeny mice of the positive F1 generation of mice in Example 1, which were heterozygotes) were isolated. Human CD34+ hematopoietic stem cells HSC (huHSC, purchased from Miao Tong Biological Science & Technology Co., Ltd.) were injected into mice by means of tail vein injection for the reconstitution of a human immune system.

K562 cells, the human leukemia cells, at logarithmic growth phase were adjusted to a concentration of $5 \times 10^3/50$ μL/well and added into 96-well plates, and sorted by human CD56 positive cell separation magnetic beads (purchased from Miltenyi Biotec) to sort reconstituted NK cells in the spleen of NCG-IL15 mice. Each well was added with 50 μL of NK cells according to the NK: K562 effector-target ratio of 2:1, 5:1, 10:1 and mixed evenly. The 96-well plates were cultured for 4 hours in an incubator at 37° C., and the killing effects of NK cells to K562 were detected by LDH (purchased from Abcam). The results were shown in FIG. 12A. With the increase of effector-target ratio, the killing rate of K562 cells by NK cells reconstituted in NCG-IL15 humanized mice also increased.

Raji cells, the human lymphoma cells at logarithmic growth phase, were adjusted to a concentration of $5 \times 10^3/50$ μL/well and added into 96-well plates, into which 0 μg/mL and 10 μg/mL of Rituximab (a targeting CD20 antibody, purchased from Roche, which kills CD20+ tumor cells mainly through the antibody-dependent cell-mediated cytotoxicity ADCC) was respectively added and cultured for 1 hour in an incubator at 37° C. They were sorted by human CD56 positive cell separation magnetic beads (purchased from Miltenyi Biotec) to sort reconstituted NK cells in the spleen of NCG-IL15 mice. Each well was added with 50 μL of NK cells according to the NK: Raji effector-target ratio of 2:1, 5:1, into 50 μL Raji cells after incubation with antibodies and mixed evenly. The 96-well plates were cultured for 4 hours in an incubator at 37° C., and the ADCC killing effects to Raji cells mediated by Rituximab antibodies were detected by LDH (purchased from Abcam). The results were shown in FIG. 12B. With the increase of effector-target ratio, the killing rate of Raji cells by NK cells reconstituted in NCG-IL15 humanized mice also increased.

Example 6. NCG-IL15 Mice Transplanted with Human Hematopoietic Stem Cells (HSCs) Used for Evaluation of Antitumor Efficacy HCC827 cells, the human non-small cell lung cancer cells, at logarithmic growth phase were collected and adjusted to a concentration of $1 \times 10^{7/100}$ μL/mouse and inoculated subcutaneously into NCG-IL15 mice and NCG-IL15 mice transplanted with human hematopoietic stem cells (HSCs), respectively. After the cells were inoculated to be tumor, the body weight was weighed twice a week. The tumor volume was measured twice a week, which was calculated as follows: tumor volume (mm³)=0.5×(long diameter of the tumor×short diameter of the tumor²). At the end of the experiment, the immune cell reconstitution in the peripheral blood of NCG-IL15 mice transplanted with human hematopoietic stem cells (HSCs) and the infiltration of immune cells in HCC827 tumor tissues formed subcutaneously were detected by flow cytometry.

Figure 13C:
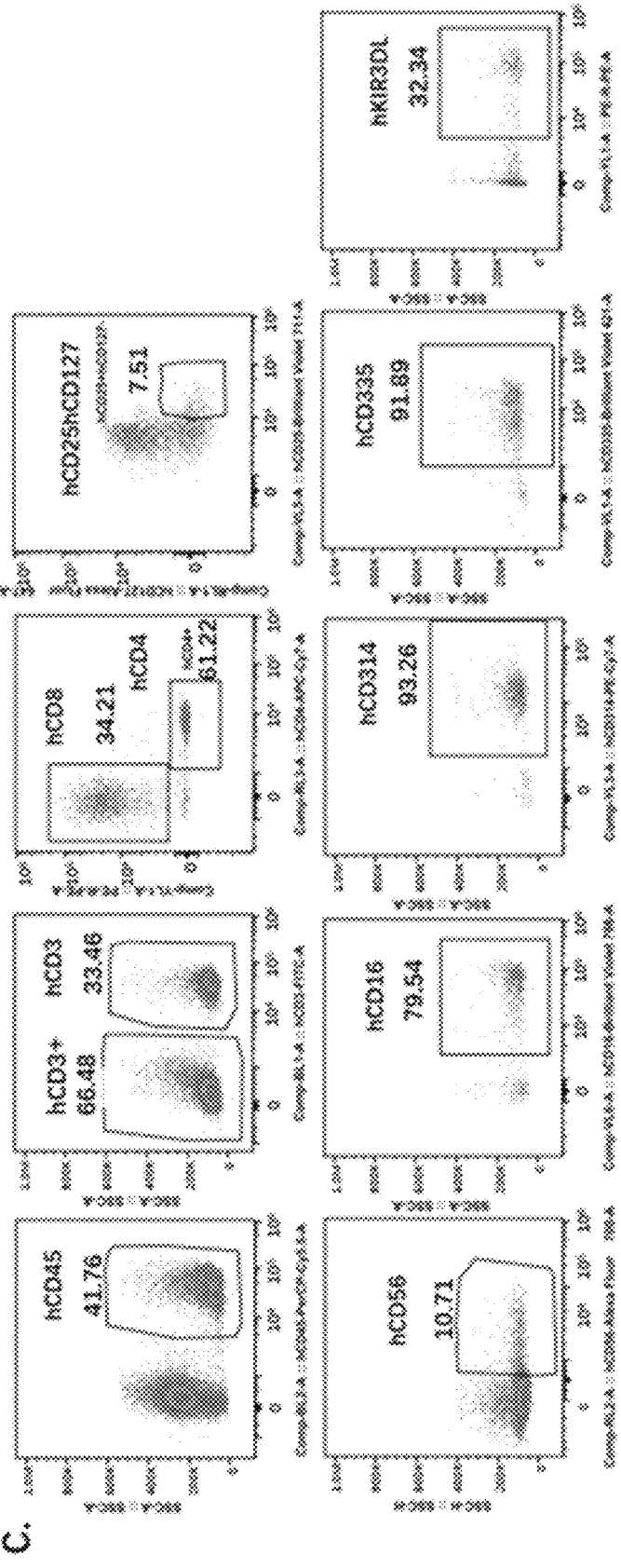
Figure 13D:
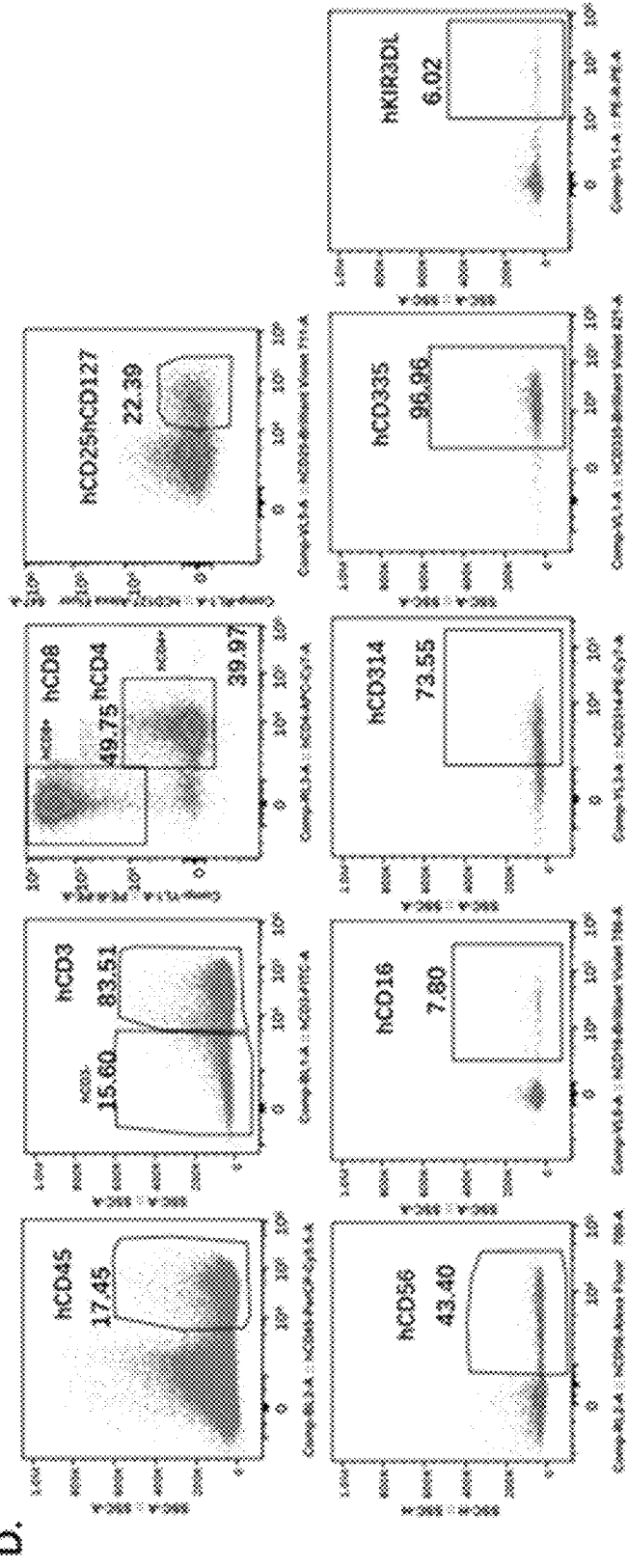

The results were shown in FIG. 13. HCC827 cells showed good tumorigenicity in both NCG-IL15 mice and NCG-IL15 mice transplanted with human hematopoietic stem cells (HSCs), and the average tumor volume reached over 900 mm³ 40 days after inoculation; no mice died during 40 days of observation, and there was no significant weight loss in mice, suggesting that the immune reconstitution did not affect the tumorigenicity of HCC827 cells and the status of mice. At the end of the experiment, the peripheral blood of NCG-IL15 mice transplanted with human hematopoietic stem cells (HSCs) was detected by flow cytometry, showing that the proportion of human hCD45+ leukocytes overpassed 20%, and they can be differentiated into high proportions of hCD3+T cells and hCD3-hCD56+NK cells; wherein, CD3+T cells can be differentiated into hCD4+ and hCD8+ cells, and a certain proportion of hCD25+hCD127- regulatory T cells can also be detected in CD4+ cells; hCD56+NK cells can express functional markers (hCD16, hKIR3DL, hCD335, hNKG2D/CD314). Meanwhile, at the end of the experiment, the tumor tissues in NCG-IL15 mice transplanted with human hematopoietic stem cells (HSCs) were detected by flow cytometry, showing that there was a large infiltration of human hCD45+ cells, including hCD3+T cells and subtype cells thereof as well as hCD3-hCD56+NK cells that can express functional markers. The above data showed that NCG-IL15 mice transplanted with human hematopoietic stem cells (HSCs) can be used to evaluate the construction of tumor models of tumor immunotherapy-related efficacies with the help of T cells and NK cells to exert anti-tumor effects.

Raji cells, the human lymphoma cells, at logarithmic growth phase were collected and adjusted to a concentration of $1 \times 10^7/100$ μL/mouse and inoculated subcutaneously into NCG-IL15 mice transplanted with human hematopoietic stem cells (HSCs). When tumors grew to an average volume of about 40 to 50 mm³, the mice were randomly divided into a PBS group, a Rituximab dosing group and a Blincyto (a bispecific antibody targeting CD3 and CD19, purchased from Biointron, mainly through mediating CD3+T cells to kill CD19+ tumor cells) dosing group, and treated using corresponding drugs. PBS and Rituximab were administrated once every 3 days, totally for 5 times; and Blincyto was administrated once a day, totally for 5 times.

Figure 14:
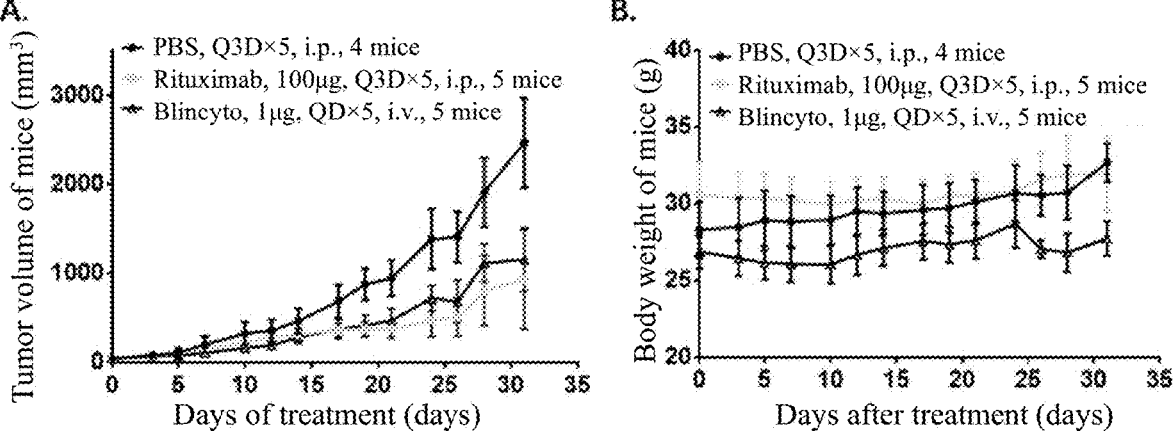

The results were shown in FIG. 14. Rituximab group and Blincyto group had inhibitory effects on tumor growth on the Raji cell tumor-bearing mice of NCG-IL15 transplanted with human hematopoietic stem cells (HSCs) (TGI of Rituximab treatment group=59.67%, TGI of Blincyto treatment group=48.95%). The above results showed that animal models constructed from NCG-IL15 mice transplanted with human hematopoietic stem cells (HSCs) in combination with human-derived tumors can be used to evaluate the tumor immunotherapy-related efficacies with the help of T cells and NK cells to exert anti-tumor effects.

The foregoing detailed description is provided by way of explanation and examples, and is not intended to limit the scope of the appended claims. Various changes of the embodiments listed herein are obvious to those of ordinary skills in the art, and are reserved within the scope of the appended claims and their equivalents.

What is claimed is:

1. A mouse, comprising a humanized Interleukin-15 (IL-15) gene, wherein the humanized IL-15 gene comprises a human IL-15 gene segment and a mouse IL-15 gene segment,
   wherein the human IL-15 gene segment comprises a portion of exon 4, exon 5, exon 6, exon 7, and a portion of exon 8 of the human IL-15 gene,
   wherein the human IL-15 gene segment comprises the nucleic acid sequence of SEQ ID NO: 1, and
   wherein the mouse IL-15 gene segment comprises exon 1, exon 2 and exon 3 of the mouse IL-15 gene.

2. The mouse according to claim 1, wherein the mouse IL-15 gene segment further comprises a regulatory sequence of the mouse IL-15 gene.

3. The mouse according to claim 1, wherein the mouse is an NOD-Prkdc$^{em26Cd52}$IL2rg$^{em26Cd22}$/NjuCrl (NCG) mouse.

4. The mouse according to claim 1, wherein the mouse IL-15 gene segment comprises a nucleotide sequence encoding a portion of signal peptide of the mouse IL-15.

5. The mouse according to claim 4, wherein said nucleotide sequence encoding a portion of signal peptide of the mouse IL-15 comprises the nucleotide sequence of SEQ ID NO: 3.

6. The mouse according to claim 1, wherein the mouse IL-15 gene segment comprises a nucleotide sequence encoding 5' untranslated region (5'UTR).

7. The mouse according to claim 6, wherein the nucleotide sequence encoding 5'UTR comprises the nucleotide sequence of SEQ ID NO: 4.

8. The mouse according to claim 1, wherein the mouse IL-15 gene segment comprises a nucleotide sequence encoding 3' untranslated region (3'UTR).

9. The mouse according to claim 8, wherein the nucleotide sequence encoding 3'UTR comprises the nucleotide sequence of SEQ ID NO: 5.

10. A cell line or a primary cell culture, which is obtained from the mouse according to claim 1.

11. A method for preparing a genetically modified mouse, comprising the steps of:

(a) modifying a fertilized mouse egg or a mouse embryonic stem (ES) cell by replacing a mouse interleukin-15 (IL-15) gene segment encoding a mature mouse IL-15 polypeptide on an endogenous mouse IL-15 locus with a human IL-15 gene segment encoding a mature human IL-15 polypeptide so as to form a humanized IL-15 gene, wherein the human IL-15 gene segment comprises a portion of exon 4, exon 5, exon 6, exon 7, and a portion of exon 8 of the human IL-15 gene, and wherein the human IL-15 gene segment comprises the nucleic acid sequence of SEQ ID NO: 1; (b) obtaining a modified fertilized mouse egg or ES cell from step (a); and (c) generating a mouse from the modified fertilized egg or ES cell obtained in step (b).

12. The method according to claim 11, wherein a mouse IL-15 gene segment remaining after replacement of the nucleotide sequence encoding the mature mouse IL-15 polypeptide comprises exon 1, exon 2 and exon 3 of the mouse IL-15 gene.

13. The method according to claim 11, wherein the mouse IL-15 gene segment further comprises a regulatory sequence of the mouse IL-15 gene.

14. The method according to claim 11, wherein the mouse is an NOD-Prkdc$^{em26Cd52}$IL2rg$^{em26Cd22}$/NjuCrl (NCG) mouse.

15. The method according to claim 11, wherein the replacement comprises using a CRISPR associated protein 9-guide RNA (Cas9-gRNA) system.

16. The method according to claim 15, wherein a guide RNA (gRNA) complementary to exon 4 of the mouse IL-15 gene comprises the nucleotide sequence of SEQ ID NO: 10; and a gRNA complementary to exon 8 of the mouse IL-15 gene comprises the nucleotide sequence of SEQ ID NO: 13; or,
   a gRNA complementary to exon 4 of the mouse IL-15 gene comprises the nucleotide sequence of SEQ ID NO: 11; and a gRNA complementary to exon 8 of the mouse IL-15 gene comprises the nucleotide sequence of SEQ ID NO: 12.

* * * * *